(12) United States Patent
Graham et al.

(10) Patent No.: US 7,256,292 B2
(45) Date of Patent: Aug. 14, 2007

(54) FLUORESCENT DYE COMPOUNDS, CONJUGATES AND USES THEREOF

(75) Inventors: Ronald J. Graham, San Ramon, CA (US); Ruiming Zou, Foster City, CA (US); Krishna G. Upadhya, Union City, CA (US); Scott C. Benson, Alameda, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 11/229,012

(22) Filed: Sep. 16, 2005

(65) Prior Publication Data

US 2006/0167257 A1    Jul. 27, 2006

Related U.S. Application Data

(60) Provisional application No. 60/611,119, filed on Sep. 16, 2004.

(51) Int. Cl.
*C07D 219/06*    (2006.01)
*C07D 221/18*    (2006.01)

(52) U.S. Cl. ............................. 546/102; 546/61; 546/58

(58) Field of Classification Search ................ 546/102, 546/61, 58
See application file for complete search history.

(56) References Cited

U.S. PATENT DOCUMENTS

| 4,810,636 A | 3/1989 | Corey |
| 5,393,615 A | 2/1995 | Corey et al. |
| 2003/0162213 A1 | 8/2003 | Fuller et al. |

FOREIGN PATENT DOCUMENTS

| EP | 0270946 A2 | 6/1988 |
| EP | 0459536 A1 | 12/1991 |
| EP | 0270946 B1 | 5/1992 |
| EP | 0459536 B1 | 9/1996 |
| WO | WO03/020734 A2 | 3/2003 |
| WO | WO2004/020603 A2 | 3/2004 |
| WO | WO2004/020603 A3 | 3/2004 |
| WO | WO2004/072304 A1 | 8/2004 |
| WO | WO2004072297 A2 | 8/2004 |

*Primary Examiner*—Charanjit S. Aulakh
(74) *Attorney, Agent, or Firm*—Vincent P. Liptak

(57) ABSTRACT

The present teachings generally relate to fluorescent dyes, linkable forms of fluorescent dyes, energy transfer dyes, reagents labeled with fluorescent dyes and uses thereof.

114 Claims, 10 Drawing Sheets

FLUORESCENT DYE COMPOUNDS, CONJUGATES AND USES THEREOF

This application claims a priority benefit under 35 U.S.C. § 119(e) from U.S. Patent Application No. 60/611,119, filed Sep. 16, 2004, which is incorporated herein by reference.

The present teachings generally relate to fluorescent dyes, linkable forms of fluorescent dyes, energy transfer dyes, and reagents labeled with fluorescent dyes, and uses thereof.

The non-radioactive detection of biological analytes utilizing fluorescent labels is an important technology in modern molecular biology. By eliminating the need for radioactive labels, safety is enhanced and the environmental impact and costs associated with reagent disposal is greatly reduced. Examples of methods utilizing such non-radioactive fluorescent detection include 4-color automated DNA sequencing, oligonucleotide hybridization methods, and detection of polymerase-chain-reaction products, immunoassays, and the like.

In many applications it is advantageous to employ multiple spectrally distinguishable fluorescent labels in order to achieve independent detection of a plurality of spatially overlapping analytes, e.g., single-tube multiplex DNA probe assays and 4-color automated DNA sequencing methods. In the case of multiplex DNA probe assays, by employing spectrally distinguishable fluorescent labels, the number of reaction tubes may be reduced thereby simplifying experimental protocols and facilitating the production of application-specific reagent kits. In the case of 4-color automated DNA sequencing, multicolor fluorescent labeling allows for the analysis of multiple bases in a single lane thereby increasing throughput over single-color methods and reducing uncertainties associated with inter-lane electrophoretic mobility variations.

Currently available multiplex dye sets suitable in 4-color automated DNA sequencing applications require blue or blue-green laser light to adequately excite fluorescence emissions from all of the dyes making up the set, e.g., argon-ion lasers. Use of blue or blue-green lasers in commercial automated DNA sequencing systems are often disadvantageous because of the high cost and limited lifetime of such lasers.

Thus, there exists a need for fluorescent dye compounds that satisfy the above constraints and are excitable by light having a wavelength above about 600 nm.

It has now been found that red fluorescence emitting dyes based on the structure (1) are very chemically and photoactively stable and are excitable by light of longer wavelengths.

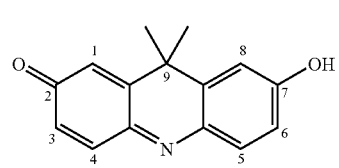
(1)

In some embodiments, the present teachings provide novel fluorescent dyes comprising a structure selected from,

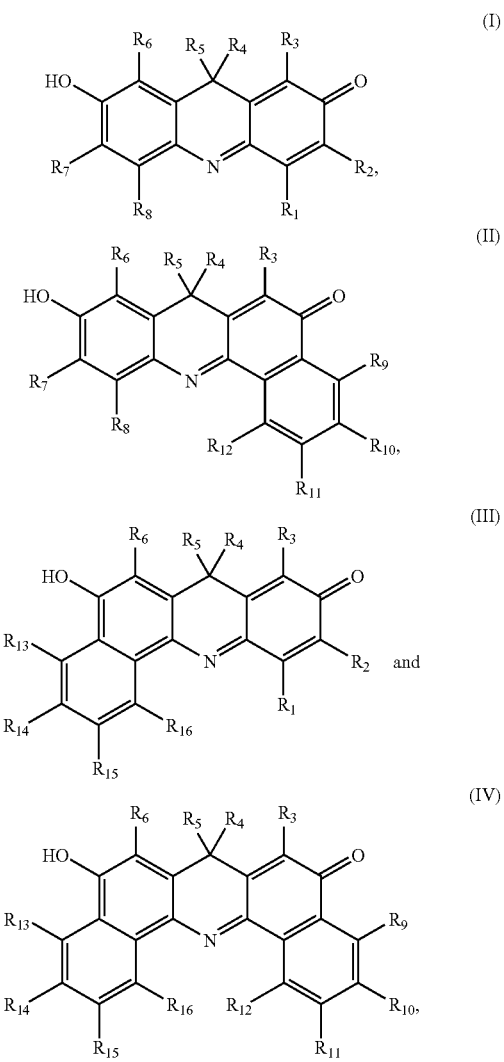

wherein $R_1$-$R_3$ and $R_6$-$R_{16}$ can each independently be —H, halogen, fluorine, chlorine, bromine, aryl, substituted aryl, heteroaryl, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkoxyaryl, substituted $C_1$-$C_6$ alkoxyaryl, phenly, substituted phenyl, substituted biphenyl, benzyl, substituted benzyl, benzoyl, substituted benzoyl, bond or linking group, wherein R can be $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkoxyaryl, substituted $C_1$-$C_6$ alkoxyaryl, phenyl, substituted phenyl, biphenyl, substituted biphenyl, benzyl, substituted benzyl, benzoyl, substituted benzoyl, bond or linking group; and $R_4$ and $R_5$ taken separately can be $C_1$-$C_6$ alkyl, $C_1$-$C_6$ substituted alkyl, $R_4$ and $R_5$ taken together can be $C_3$-$C_7$ cycloalkyl, $C_4$-$C_7$ unsaturated cycloalkyl, $C_3$-$C_7$ substituted cycloalkyl or $C_4$-$C_7$ substituted unsaturated cycloalkyl;

with the proviso that if the compound comprises the structure (I), then at least one of $R_1$-$R_3$ or $R_8$ is not —H. Optionally, at least one of $R_1$-$R_3$ and $R_6$-$R_{16}$ can be —$SO_3H$.

In some embodiments, the present teachings provide for energy transfer dye compounds comprising a donor dye covalently attached to an acceptor dye, wherein the donor dye is capable of absorbing light at a first wavelength and emitting excitation energy in response, and the acceptor dye is capable of absorbing the excitation energy emitted by the donor dye and fluorescing at a second wavelength in response. In some embodiments, the donor dye can be covalently attached to the acceptor dye by a bond, a non-nucleotidic linker or a nucleotidic linker (i.e. -a polynucleotide, ribonucleic acid, and the like). In some embodiments, the linker can serve to facilitate efficient transfer of energy between the donor dye and the acceptor dye. In some embodiments, at least one of the donor and acceptor dyes is a dye of the present teachings.

In some embodiments, the present teachings provide for labeled nucleosides and/or nucleotides comprising the structure

NUC-L-D wherein NUC comprises a nucleoside, a nucleotide, a modified nucleoside or a modified nucleotide, L comprises a bond or a linker and D comprises a dye compound of the present teachings. In some embodiments, NUC and D can be covalently linked by a linking moiety, L, wherein L can be attached to D at one of $R_1$-$R_3$ and $R_6$-$R_{16}$. In some embodiments, if NUC comprises a purine base, the linking moiety can be attached to the 8-position of the purine, if NUC comprises a 7-deazapurine base, the linking moiety can be attached to the 7-position of the 7-deazapurine, and if NUC comprises a pyrimidine base, the linking moiety can be attached to the 5-position of the pyrimidine.

In some embodiments, the present teachings provide for oligonucleotide analysis methods comprising the steps of forming a set of labeled oligonucleotide fragments labeled with a dye of the structure set forth above, subjecting the labeled oligonucleotide fragments to a size-dependent separation process, e.g., electrophoresis, and detecting the labeled oligonucleotide fragments subsequent to the separation process.

These and other features and advantages of the present teachings will become better understood with reference to the following description, figures, and appended claims.

Figure 1:
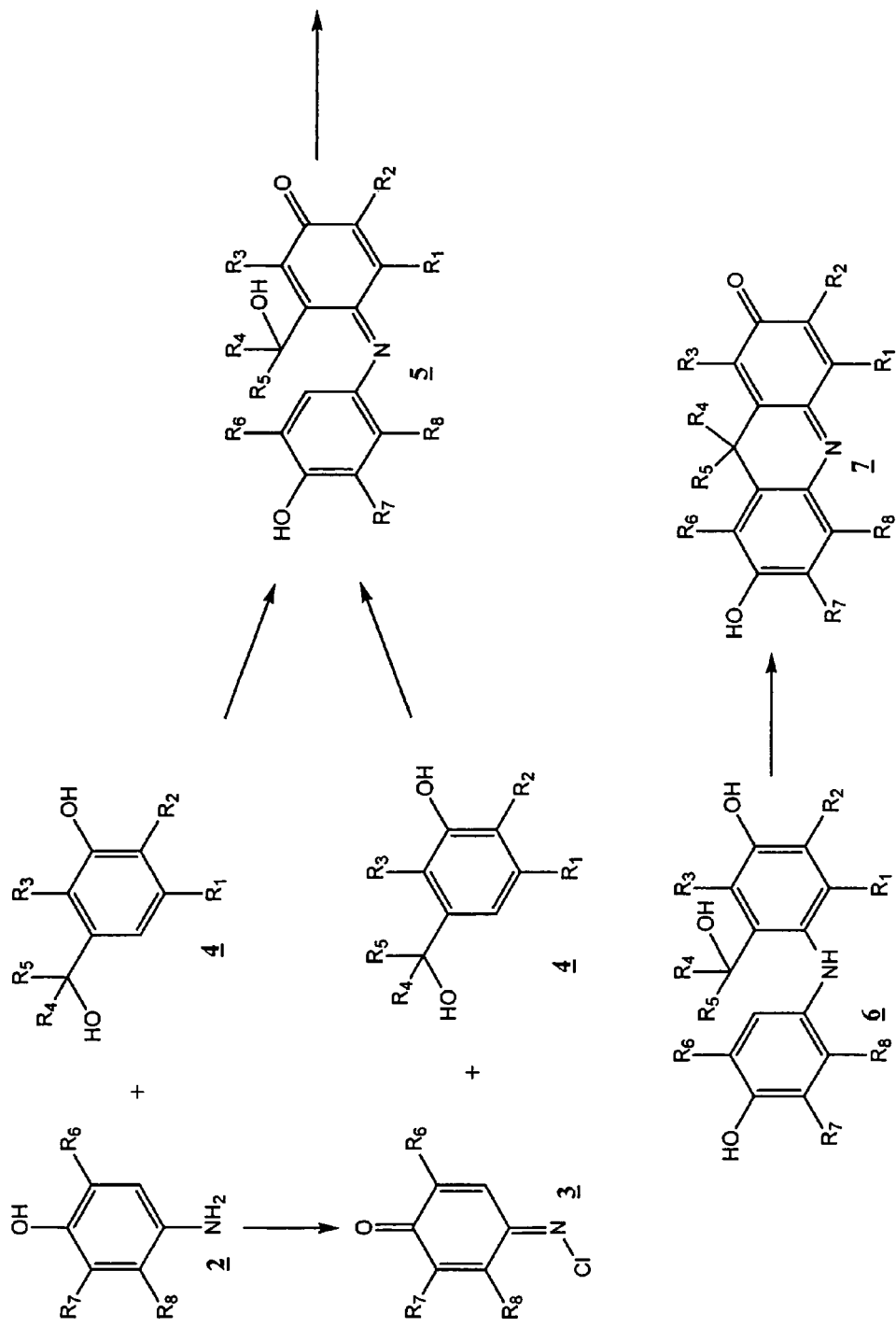
FIG. 1 shows a generalized synthetic pathway for the synthesis of dye compounds of the present teachings comprising the structure (I).

Reference will now be made in detail to alternative embodiments of the present teachings, examples of which are illustrated in the accompanying drawings. While the present teachings will be described in conjunction with the alternative embodiments, it will be understood that they are not intended to limit the present teachings to those embodiments. On the contrary, the present teachings are intended to cover all alternatives, modifications, and equivalents, which may be included within the invention as defined by the appended claims.

In this application, the use of the singular includes the plural unless specifically stated otherwise. In this application, the use of "or" means "and/or" unless stated otherwise. Furthermore, the use of the term "comprising," as well as other forms, such as "comprises" and "comprise," will be considered inclusive, in that the term "comprising" leaves open the possibility of including additional elements.

It will be understood that the chemical structures that are used to define compounds of the present teachings are each representations of one of the possible resonance structures that each given structure can be represented by. Further, it will be understood that by definition, resonance structures are merely a graphical representation used by those of skill in the art to represent electron delocalization, and that the present teachings are not limited in any way by showing one particular resonance structure for a given structure.

Generally, the present teachings comprise fluorescent dye compounds useful as fluorescent labels, as components of energy transfer dyes, in conjugates of nucleosides, nucleotides and polynucleotides, in methods utilizing such dyes and reagents in the area of analytical biotechnology. The compounds of the present teachings may find particular application in the area of fluorescent nucleic acid analysis, e.g., automated DNA sequencing and fragment analysis, detection of probe hybridization in hybridization arrays, detection of nucleic acid amplification products, and the like.

In some embodiments, the present teachings provide novel fluorescent dyes comprising a structure selected from,

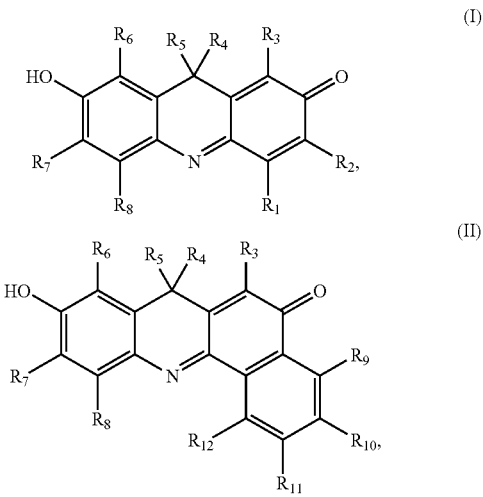

-continued

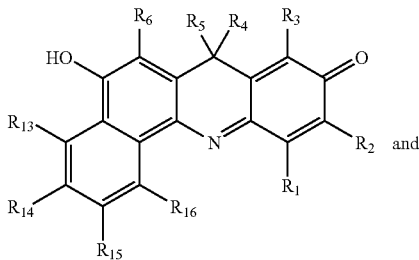

(III)

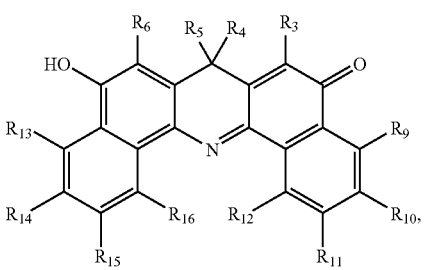

(IV)

wherein

R$_1$-R$_3$ and R$_6$-R$_{16}$ can each independently be —H, halogen, fluorine, chlorine, bromine, aryl, substituted aryl, heteroaryl, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR, —NO$_2$, C$_1$-C$_6$ alkyl, substituted C$_1$-C$_6$ alkyl, C$_1$-C$_6$ alkoxy, substituted C$_1$-C$_6$ alkoxy, C$_1$-C$_6$ alkoxyaryl, substituted C$_1$-C$_6$ benzyl, benzoyl, substituted benzoyl, bond or linking group, wherein R can be C$_1$-C$_6$ alkyl, substituted C$_1$-C$_6$ alkyl, C$_1$-C$_6$ alkoxy, substituted C$_1$-C$_6$ alkoxy, C$_1$-C$_6$ alkkoxyaryl, substituted C$_1$-C$_6$ alkoxyaryl, phenyl, substituted phenyl, biphenyl, substituted biphenyl, benzyl, substituted benzyl, benzoyl, substituted benzoyl, bond or linking group; and R$_4$ and R$_5$ taken separately can be C$_1$-C$_6$ alkyl, C$_1$-C$_6$ substituted alkyl, R$_4$ and R$_5$ taken together can be C$_3$-C$_7$ cycloalkyl, C$_4$-C$_7$ unsaturated cycloalkyl, C$_3$-C$_7$ substituted cycloalkyl or C$_4$-C$_7$ substituted unsaturated cycloalkyl;

with the proviso that if the compound comprises the structure (I), then at least one of R$_1$-R$_3$ or R$_8$ is not —H. Optionally, at least one of R$_1$-R$_3$ and R$_6$-R$_{16}$ can be —SO$_3$H. It will be understood that any of the compounds described herein can include the phenol oxygen deprotonated form as well as all possible resonance structures.

In some embodiments, dye compounds of the present teachings can comprise the structure:

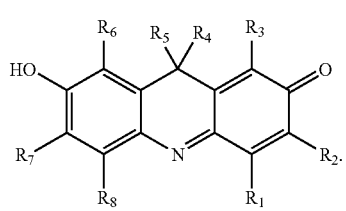

(I)

In some embodiments, dye compounds of the present teachings can comprise the structure:

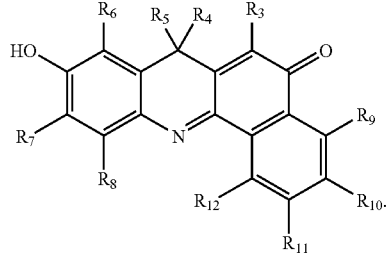

(II)

In some embodiments, dye compounds of the present teachings can comprise the structure:

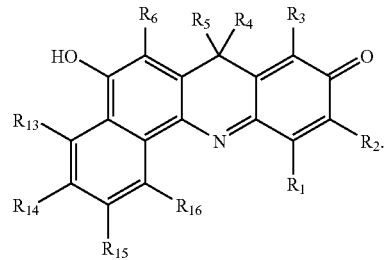

(III)

In some embodiments, dye compounds of the present teachings can comprise the structure:

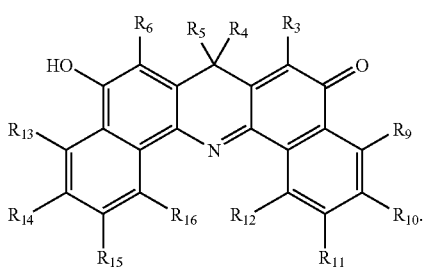

(IV)

In some embodiments, R$_6$ and R$_7$ can each independently be halogen, fluorine, chlorine or bromine. In some embodiments, R$_6$ and R$_7$ can be fluorine. In some embodiments, R$_6$ and R$_7$ can be chlorine. In some embodiments, R$_6$ and R$_7$ can be bromine.

In some embodiments, R$_6$ can be —H and R$_7$ can be —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$,and —CH$_2$NHR where R is defined as above. In some embodiments, X$_1$ can be —H and X$_2$ can be —H, —SO$_3$H, —SO$_3$R, —CH$_2$CO$_2$H, —CH$_2$CO$_2$R, —CH$_2$NH$_2$, and —CH$_2$NHR where R is define as above.

In some embodiments, dye compounds of the present teachings comprise the structure (I), wherein R$_1$-R$_3$ and R$_8$ can each independently be —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR or —NO$_2$, wherein R is defined as above, with the proviso that if the compound comprises the structure (I), then at least one of $R_1$-$R_3$ or $R_8$ is not —H. In some embodiments, $R_1$-$R_3$ and $R_8$ can each independently be —$SO_3H$, —$SO_3R$, —$CH_2NH_2$, —$CH_2NHR$ or —$NO_2$, wherein R is defined as above. In some embodiments, $R_1$-$R_3$ and $R_8$ can each independently be —$SO_3H$ or —$SO_3R$, wherein R is defined as above. In some embodiments, $R_1$-$R_3$ and $R_8$ can each independently be —$CH_2NH_2$ or —$CH_2NHR$, wherein R is defined as above.

In some embodiments, dye compounds of the present teachings comprise the structure (I), wherein $R_6$ and $R_7$ can each independently be halogen, fluorine, chlorine or bromine and $R_1$-$R_3$ and $R_8$ can each independently be —H, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkoxyaryl, substituted $C_1$-$C_6$ alkoxyaryl, phenyl, substituted phenyl, biphenyl, substituted biphenyl, benzyl, substituted benzyl, benzoyl, substituted benzoyl, bond or linking group, wherein R is defined as above, with the proviso that if the compound comprises the structure (I), then at least one of $R_1$-$R_3$ or $R_9$ is not —H. In some embodiments, $R_6$ and $R_7$ can each independently be halogen, fluorine, chlorine or bromine and $R_1$-$R_3$ and $R_8$ can each independently be —$SO_3H$, —$SO_3R$, —$CH_2NH_2$, —$CH_2NHR$ or —$NO_2$, wherein R is defined as above. In some embodiments, $R_6$ and $R_7$ are fluorine and $R_1$-$R_3$ and $R_8$ can each independently be —$SO_3H$, —$SO_3R$, —$CH_2NH_2$, —$CH_2NHR$ or —$NO_2$, wherein R is defined as above. In some embodiments, $R_6$ and $R_7$ are chlorine and $R_1$-$R_3$ and $R_9$ can each independently be —$SO_3H$, —$SO_3R$, —$CH_2NH_2$, —$CH_2NHR$ or —$NO_2$, wherein R is defined as above. In some embodiments, $R_6$ and $R_7$ are bromine and $R_1$-$R_3$ and $R_8$ can each independently be —$SO_3H$, —$SO_3R$, —$CH_2NH_2$, —$CH_2NHR$ or —$NO_2$, wherein R is defined as above.

In some embodiments, dye compounds of the present teachings can comprise the structure (I), wherein $R_6$ can be —H and $R_7$ can be —H, —$SO_3H$, —$SO_3R$, —$CH_2CO_2H$, —$CH_2CO_2R$, —$CH_2NH_2$, or —$CH_2NHR$, wherein R is defined as above, and $R_1$-$R_3$ and $R_9$ can each independently be —$SO_3H$, —$SO_3R$, —$CH_2NH_2$, —$CH_2NHR$, or —$NO_2$, wherein R is defined as above. In some embodiments, $R_6$ can be —H and $R_7$ can be —H, —$SO_3H$ or —$SO_3R$, and $R_1$-$R_3$ and $R_8$ can each independently be —$CH_2NH_2$ or —$CH_2NHR$, wherein R is defined as above.

In some embodiments, a dye compound of the present teachings can comprise the structure

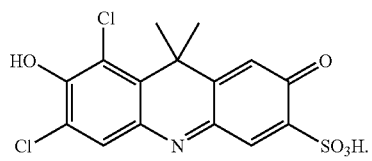

In some embodiments, a dye compound of the present teachings can comprise the structure

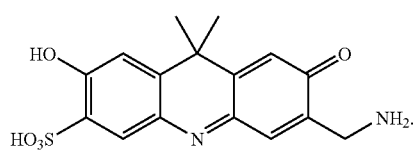

In some embodiments, a dye compound of the present teachings can comprise the structure

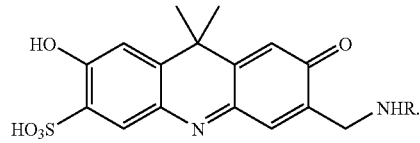

In some embodiments, R can be substituted benzoyl. In some embodiments, R can be linking group. In some embodiments, R can be trifluoroacetyl. In some embodiments, R can comprise the structure

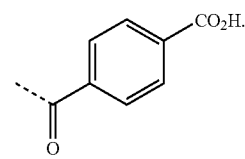

In some embodiments, R can comprise the structure

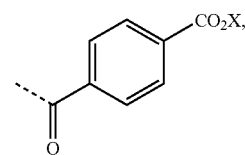

X can be succinimide.

In some embodiments, R can be

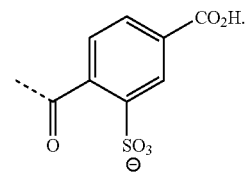

In some embodiments, $R_4$ and $R_5$ can be methyl. In some embodiments, at least one of $R_2$ and $R_3$ can be —$NO_2$ and $R_4$ and $R_5$ can be methyl.

In some embodiments, dye compounds of the present teachings can comprise the structure (II), wherein $R_6$ and $R_7$ can each independently be halogen, fluorine, chlorine or bromine, R can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$. In some embodiments, dye compounds of the present teachings can comprise the structure (II), wherein $R_6$ and $R_7$ can each independently be halogen, fluorine, chlorine or bromine and any of $R_3$, $R_8$ and $R_9$-$R_{12}$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkoxyaryl, substituted $C_1$-$C_6$ alkoxyaryl, phenyl, substituted phenyl, biphenyl, substituted biphenyl, benzyl, substituted benzyl, benzoyl, substituted benzoyl, bond or linking group, wherein R is defined as above.

In some embodiments, dye compounds of the present teachings can comprise the structure (II), wherein $R_6$ and $R_7$ can each independently be halogen, fluorine, chlorine or bromine, $R_9$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$, and $R_{10}$-$R_{12}$ can be —H, wherein R is defined as above. In some embodiments, dye compounds of the present teachings can comprise the structure (II), wherein $R_6$ and $R_7$ can each independently be halogen, fluorine, chlorine or bromine, $R_{10}$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$, and $R_9$ and $R_{11}$-$R_{12}$ can be —H, wherein R is defined as above. In some embodiments, dye compounds of the present teachings can comprise the structure (II), wherein $R_6$ and $R_7$ can each independently be halogen, fluorine, chlorine or bromine, $R_{11}$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$, and $R_9$-$R_{10}$ and $R_{12}$ can be —H, wherein R is defined as above. In some embodiments, dye compounds of the present teachings can comprise the structure (II), wherein $R_6$ and $R_7$ can each independently be halogen, fluorine, chlorine or bromine, $R_{12}$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$, and $R_9$-$R_{11}$ can be —H, wherein R is defined as above.

In some embodiments, dye compounds of the present teachings can comprise the structure (II), wherein $R_6$ can be —H and $R_7$ can be —H, —$SO_3H$, —$SO_3R$, —$CH_2CO_2H$, —$CH_2CO_2R$, —$CH_2NH_2$, or —$CH_2NHR$, wherein R is defined as above, $R_9$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$ and $R_{10}$-$R_{12}$ can be —H, wherein R is defined as above. In some embodiments, dye compounds of the present teachings can comprise the structure (II), wherein $R_6$ can be —H and $R_7$ can be —H, —$SO_3H$, —$SO_3R$, —$CH_2CO_2H$, —$CH_2CO_2R$, —$CH_2NH_2$, or —$CH_2NHR$, wherein R is defined as above, $R_{10}$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$, and $R_9$ and $R_{11}$-$R_{12}$ can be —H, wherein R is defined as above. In some embodiments, dye compounds of the present teachings can comprise the structure (II), wherein $R_6$ can be —H and $R_7$ can be —H, —$SO_3H$, —$SO_3R$, —$CH_2CO_2H$, —$CH_2CO_2R$, —$CH_2NH_2$, or —$CH_2NHR$, wherein R is defined as above, $R_{11}$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$, and $R_9$-$R_{10}$ and $R_{12}$ can be —H, wherein R is defined as above. In some embodiments, dye compounds of the present teachings can comprise the structure (II), wherein $R_6$ can be —H and $R_7$ can be —H, —$SO_3H$, —$SO_3R$, —$CH_2CO_2H$, —$CH_2CO_2R$, —$CH_2NH_2$, or —$CH_2NHR$, wherein R is defined as above, $R_{12}$ can be —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ or —$NO_2$ and $R_9$-$R_{11}$ can be —H, wherein R is defined as above.

In some embodiments, any of $R_9$-$R_{12}$ can be —$SO_3H$, —$SO_3R$, —$CH_2NH_2$, —$CH_2NHR$, or —$NO_2$, wherein R is defined as above. In some embodiments, any of $R_9$-$R_{12}$ can be —$SO_3H$ or —$SO_3R$, wherein R is defined as above. In some embodiments, any of $R_9$-$R_{12}$ can be —$CH_2NH_2$ or —$CH_2NHR$, wherein R is defined as above.

In some embodiments, a dye compound of the present teachings can comprise the structure

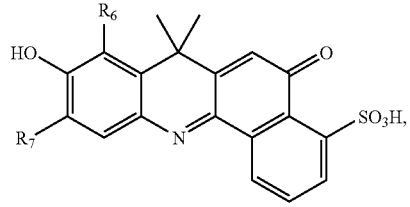

wherein $R_6$ and $R_7$ can be hydrogen, fluorine, chlorine or bromine.

In some embodiments, a dye compound of the present teachings can comprise the structure

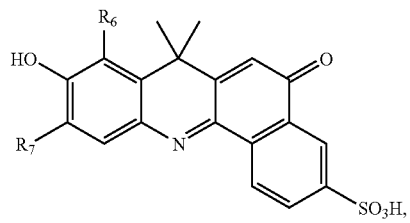

wherein $R_6$ and $R_7$ can be hydrogen, fluorine, chlorine or bromine.

In some embodiments, a dye compound of the present teachings can comprise the structure

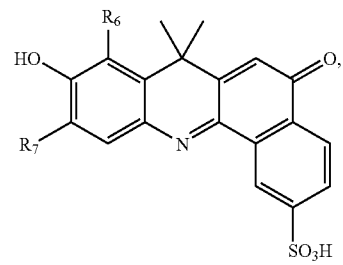

wherein $R_6$ and $R_7$ can be hydrogen, fluorine, chlorine or bromine.

In some embodiments, a dye compound of the present teachings can comprise the structure

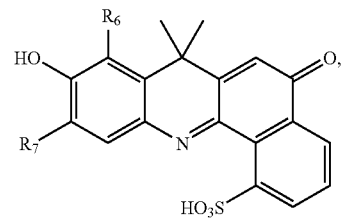

wherein $R_6$ and $R_7$ can be hydrogen, fluorine, chlorine or bromine.

In some embodiments, a dye compound of the present teachings can comprise the structure

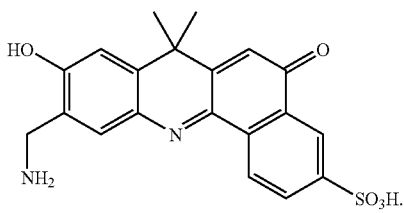

In some embodiments, a dye compound of the present teachings can comprise the structure

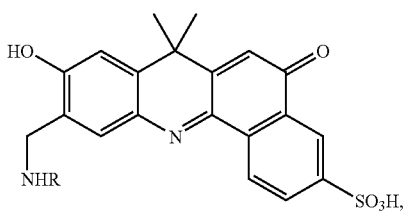

wherein R is defined as above.

In some embodiments, a dye compound of the present teachings can comprise the structure

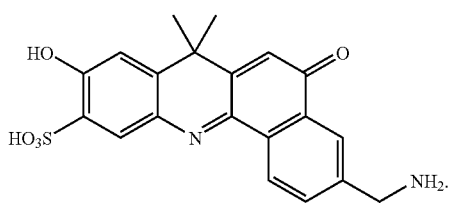

In some embodiments, a dye compound of the present teachings can comprise the structure

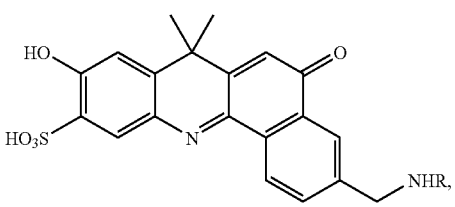

wherein R is defined as above.

In some embodiments, R can be substituted benzoyl. In some embodiments, R can be linking group. In some embodiments, R can be trifluoroacetyl. In some embodiments, R can comprise the structure

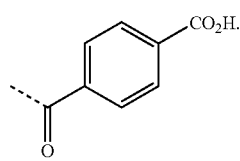

In some embodiments, R can comprise the structure

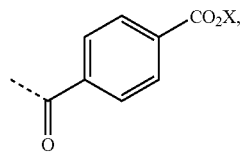

X can be succinimide.

In some embodiments, R can be

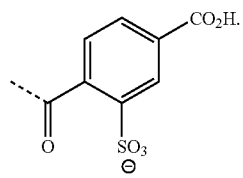

In some embodiments, compounds of the present teachings comprise the structure (III). In some embodiments, $R_1$ and $R_3$ can be —H. In some embodiments, $R_6$ can be —H. In some embodiments, $R_{13}$, $R_{15}$ and $R_{16}$ can be —H. In some embodiments, $R_2$ can be —$SO_3H$. In some embodiments, $R_2$ can be —H. In some embodiments, $R_{14}$ can be —$CH_2NH_2$. In some embodiments, $R_{14}$ can be —$CH_2NHR$. In some embodiments, R can be

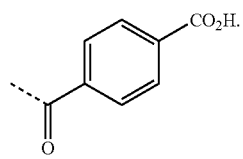

In some embodiments, R can comprise the structure

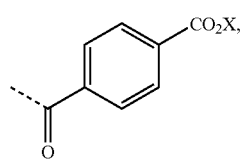

X can be succinimide.

In some embodiments, R can be

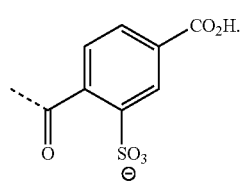

In some embodiments, R can be linking group. In some embodiments, $R_{14}$ can be —H. In some embodiments, $R_{14}$ can be —$SO_3H$. In some embodiments, $R_{14}$ can be —H. In some embodiments, $R_2$ can be —$CH_2NH_2$. In some embodiments, $R_2$ can be —$CH_2NHR$. In some embodiments, R can be

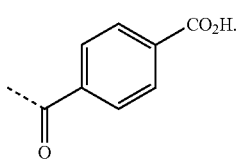

In some embodiments, R can comprise the structure

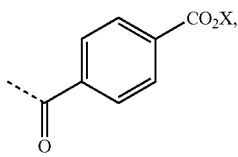

X can be succinimide.

In some embodiments, R can be

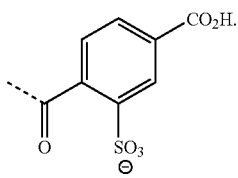

In some embodiments, R can be linking group. In some embodiments, $R_2$ can be —H. In some embodiments, $R_4$ and $R_5$ can be methyl.

In some embodiments, compounds of the present teachings comprise the structure (IV). In some embodiments, $R_{10}$ can be —$SO_3H$. In some embodiments, $R_{10}$ can be —H. In some embodiments, $R_{14}$ can be —$CH_2NH_2$. In some embodiments, $R_{14}$ can be —$CH_2NHR$. In some embodiments, R can be

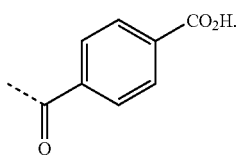

In some embodiments, R can comprise the structure

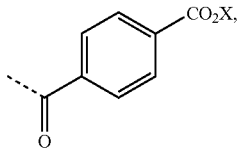

X can be succinimide.

In some embodiments, R can be

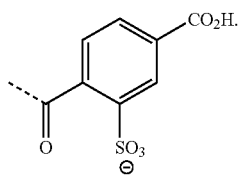

In some embodiments, R is linking group. In some embodiments, $R_{14}$ can be —H. In some embodiments, $R_3$, $R_6$, $R_9$, $R_{11}$, $R_{12}$, $R_{13}$, $R_{15}$ and $R_{16}$ can be —H. In some embodiments, $R_{14}$ can be —$SO_3H$. In some embodiments, $R_{14}$ can be —H. In some embodiments, $R_{10}$ can be —$CH_2NH_2$. In some embodiments, $R_{10}$ can be —$CH_2NHR$. In some embodiments, R can be

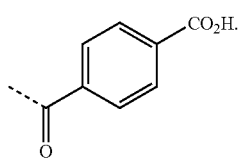

In some embodiments, R can comprise the structure

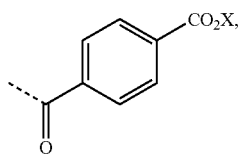

X can be succinimide.

In some embodiments, R can be

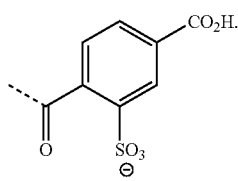

In some embodiments, R can be linking group. In some embodiments, $R_{14}$ can be —H. In some embodiments, $R_3$, $R_6$, $R_9$, $R_{11}$, $R_{12}$, $R_{13}$, $R_{15}$ and $R_{16}$ can be —H. In some embodiments, $R_4$ and $R_5$ can be methyl.

As used herein "substituted" refers to a molecule wherein one or more hydrogen atoms are replaced with one or more non-hydrogen atoms, functional groups or moieties. For example, unsubstituted amine is —$NH_2$, while a substituted amine can be —$NHCH_3$. Exemplary substituents include but are not limited to halogen, fluorine, chlorine, bromine, $C_1$-$C_6$ alkyl, $C_1$-$C_6$ cycloalkyl, $C_1$-$C_6$ branched alkyl, $C_1$-$C_6$ alkene, $C_1$-$C_6$ cyclic alkene, $C_1$-$C_6$ branched alkene, $C_1$-$C_6$ alkyne, $C_1$-$C_6$ branched alkyne, sulfate, sulfonate, sulfone, amino, ammonium, amido, nitrile, $C_1$-$C_6$ alkoxy, phenoxy, substituted phenoxy aromatic, phenyl, polycyclic aromatic, electron-rich heterocycle, and linking group.

As used herein, "linking group" refers to a moiety capable of reacting with a "complementary functionality" attached to a reagent or member of an energy transfer dye pair, such reaction forming a "linkage" connecting the dye to the reagent or member of the energy transfer dye pair. Suitable linking groups include but are not limited to isothiocyanate, sulfonyl chloride, 4,6-dichlorotriazinyl, succinimidyl ester, or other active carboxylate whenever the complementary functionality is amine. Suitable linking groups include but are not limited to maleimide, haloacetyl, iodoacetyl, haloacetamide or iodoacetamide whenever the complementary functionality is sulfhydryl. See, for example, R. Haugland, *Molecular Probes Handbook of Fluorescent Probes and Research Chemicals*, Molecular probes, Inc. (1992).

Furthermore, it will be understood that a variety of complementary linking group/complementary functionality pairs suitable for covalently conjugating dye molecules of the present teachings to various molecules or substrates (i.e.—nucleotides, nucleosides, oligonucleotides, peptides, other dyes molecules, linking moieties, and the like) are known in the art. Examples of complementary electrophiles and nucleophiles suitable for use as linking group/complementary functionality pairs in a wide variety of contexts are shown in Table 1, where the reaction of the indicated electrophilic and nucleophilic species yields the indicated covalent linkage. Conditions under which the covalent linkages are formed are well-known.

TABLE 1

Examples Of Some Routes To Useful Covalent Linkages

| Electrophilic Group | Nucleophilic Group | Resulting Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| carbonates | amines | carbamates |
| chloroformates | amine | carbamates |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amineslanilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |

TABLE 1-continued

Examples Of Some Routes To Useful Covalent Linkages

| Electrophilic Group | Nucleophilic Group | Resulting Linkage |
|---|---|---|
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COX, where X is a good leaving group, e.g., oxysuccinimidyl (—ONC$_4$H$_4$O$_2$), oxysulfosuccinimidyl (—ONC$_4$H$_3$O$_2$—SO$_3$H), 1-oxybenzotriazoiyl (—OC$_6$H$_4$N$_3$); or an aryloxy group of the formula —OR", where R" is an aryl or an aryl substituted with one or more of the same or different electron-withdrawing substituents (e.g., —NO$_2$, —F, —Cl, —CN or —CF$_3$), used to form an anhydride or mixed anhydride of the formula —OCOR$^a$ or —OCNR$^a$NHR$^b$, where R$^a$ and R$^b$, which may be the same or different, are (C$_1$-C$_6$) alkyl, (C$_1$-C$_6$) perfluoroalkyl or (C$_1$-C$_6$) alkoxy; or cyclohexyl, 3-dimethylaminopropyl, or N-morpholinoethyl.
**Acyl azides can also rearrange to isocyanates.

The selection of nucleophile or electrophile used to covalently conjugate a dye of the present teachings to a given molecule or substrate can depend upon the identity of the complementary functional group on the molecule or substrate to which the dye molecule is to be conjugated. Types of complementary functional groups that can be present on molecules or substances to be conjugated include, but are not limited to, amines, thiols, alcohols, phenols, aldehydes, ketones, phosphates, imidazoles, hydrazines, hydroxylamines, mono- and disubstituted amines, halides, epoxides, sulfonate esters, carboxylic acids or carboxylates.

In some embodiments, suitable nucleophiles for use in connection with the present teachings comprise amines, phenols, anilines, thiols or alcohols, or combinations thereof. In some embodiments, the nucleophile comprises an amine. In some embodiments, the nucleophile comprises a primary amine. In some embodiments, the nucleophile comprises a secondary amine.

In some embodiments, the electrophile comprises an acrylamide, an activated ester of a carboxylic acid, an acyl azide, an acyl nitrile, an acyl halide, an aldehyde, an alkyl halide, an anhydride, an aryl halide, an azide, an aziridine, a boronate, a carboxylic acid or carboxylate, a diazoalkane, a haloacetamide, a halotriazine, a hydrazine, an imido ester, an isocyanate, an isothiocyanate, a maleimide, a phosphoramidite a Michael acceptor (i.e.—an α,β-unsaturated ester, an α,β-unsaturated aldehyde, and the like) or a sulfonyl halide.

In some embodiments, the electrophile comprises an activated ester of a carboxylic acid or carboxylate, a succinimidyl ester, a haloacetamide, an acyl halide, an alkyl halide, a sulfonyl halide, an isothiocyanate, a maleimide or an azidoperfluorobenzamido group. In some embodiments, the linking group is a N-hydroxysuccinimidyl (NHS) ester and the complementary functionality is an amine. To form an NHS ester, a dye of the present teachings including a carboxylic acid moiety as a linking group is reacted with, for example, dicyclohexylcarbodiimide (DCC) and N-hydroxysuccinimide. Alternatively, to form an NHS ester, a molecule or substrate to be conjugated to a dye molecule of the present teachings including a carboxylic acid moiety as a linking group is reacted with, for example, dicyclohexylcarbodiimide (DCC) and N-hydroxysuccinimide.

An exemplary synthetic scheme for the preparation of compounds of the present teachings comprising the structure (I) is shown in FIG. 1. Using, for example, the synthetic procedures described in Corey, P. F., U.S. Pat. No. 4,810,636 as a guide, one of skill in the art can react a 4-hydroxyaniline compound of the type (2) with a tertiary alcohol (4), such as 2-(4'-hydroxyphenyl)-2-propanol, in the presence of a base to form compound (5). Alternatively, one can oxidize 4-hydroxyaniline compound (2) to form an N-chloroimine compound of the type (2) which can be reacted with a tertiary alcohol (4), such as 2-(4'-hydroxyphenyl)-2-propanol, in the presence of a base to form compound (5). Compound (5) can then be reacted with a reducing agent, such as sodium dithionite, to form secondary amine compound (6). Compound (6) can then be converted to compound (7) by cyclization, through treatment with an acid such as 2N HCl, followed by oxidation, with for example sodium periodate. In some embodiments, depending on the substitution pattern present, compound (7) can be optionally be further derivitized. For example, compound (2) can optionally be sulfonated by reaction with, for example, chlorosulfonic acid.

Alternatively, compound (7) can be aminomethylated by reaction with an aminomethylating agent, for example, N-(hydroxymethyl)trifluoroacetamide in the presence of an acid such as concentrated sulfuric acid, or similar established conditions.

Figure 2:
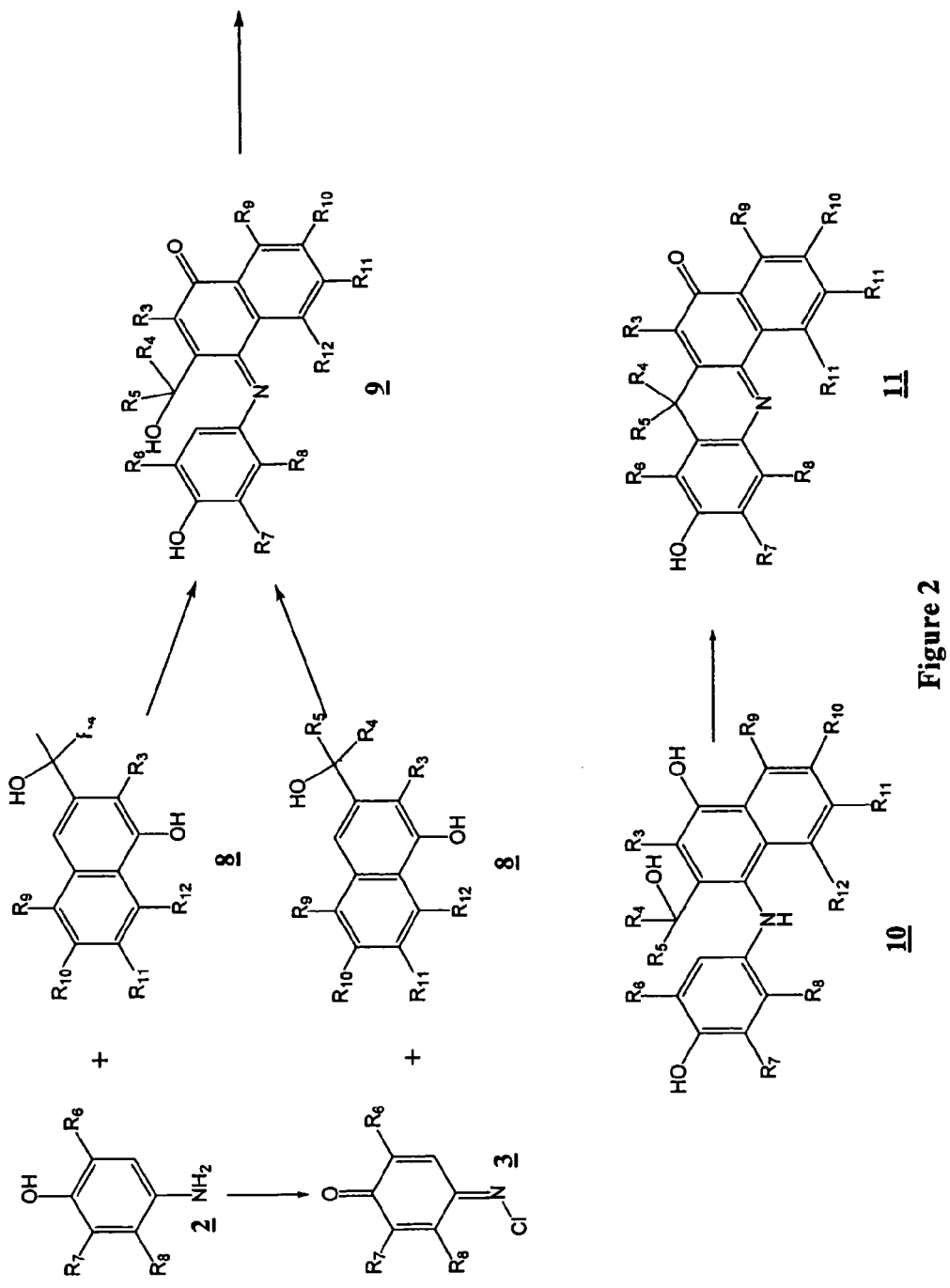
FIG. 2 shows a generalized synthetic pathway for the synthesis of dye compounds of the present teachings comprising the structure (II).

An exemplary synthetic scheme for the preparation of compounds of the present teachings comprising the structure (II) is shown in FIG. 2. Following a scheme similar to that described by Corey, a 4-hydroxyaniline compound of the type (2) can be reacted with a tertiary alcohol (8), such as 2-(4'-hydroxynathalen-2-yl)-2-propanol, in the presence of a base to form compound (2). Alternatively, 4-hydroxyaniline compound (2) can be oxidized using known conditions to form an N-chloroimine compound of the type (3) which can be reacted with a tertiary alcohol (8) in the presence of a base to form compound (2). Compound (2) can then be reacted with a reducing agent, such as sodium dithionite, to form secondary amine compound (1). Compound (10) can then be converted to compound (11) by cyclization, through treatment with an acid such as 2N HCl, followed by oxidation, with for example sodium periodate. In some embodiments, depending on the substitution pattern present, compound (11) can be optionally be further derivitized. For example, compound (11) can optionally be sulfonated by reaction with, for example, chlorosulfonic acid.

Figure 3:
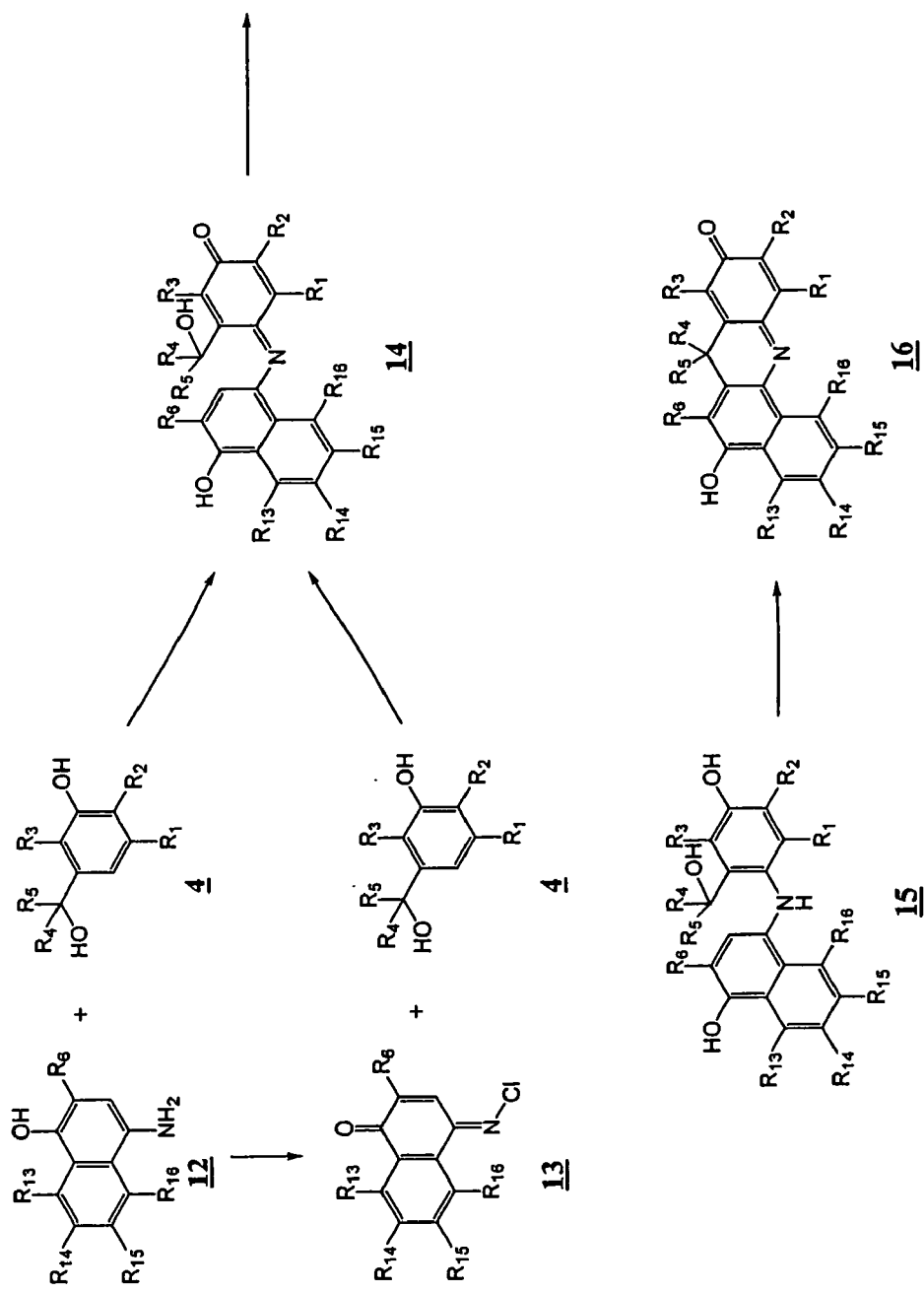
FIG. 3 shows a generalized synthetic pathway for the synthesis of dye compounds of the present teachings comprising the structure (III).

An exemplary synthetic scheme for the preparation of compounds of the present teachings comprising the structure (III) is shown in FIG. 3. Following a scheme similar to that described by Corey, a compound of the type (12) can be reacted with a tertiary alcohol (4), in the presence of a base to form compound (14). Alternatively, compound (1) can be oxidized using known conditions to form an N-chloroimine compound of the type (13) which can be reacted with a tertiary alcohol (4) in the presence of a base to form compound (14). Compound (14) can then be reacted with a reducing agent, such as sodium dithionite, to form secondary amine compound (15). Compound (15) can then be converted to compound (16) by cyclization, through treatment with an acid such as 2N HCl, followed by oxidation, with for example sodium periodate. In some embodiments, depending on the substitution pattern present, compound (16) can optionally be further derivitized. For example, compound (16) can optionally be sulfonated by reaction with, for example, chlorosulfonic acid.

Figure 4:
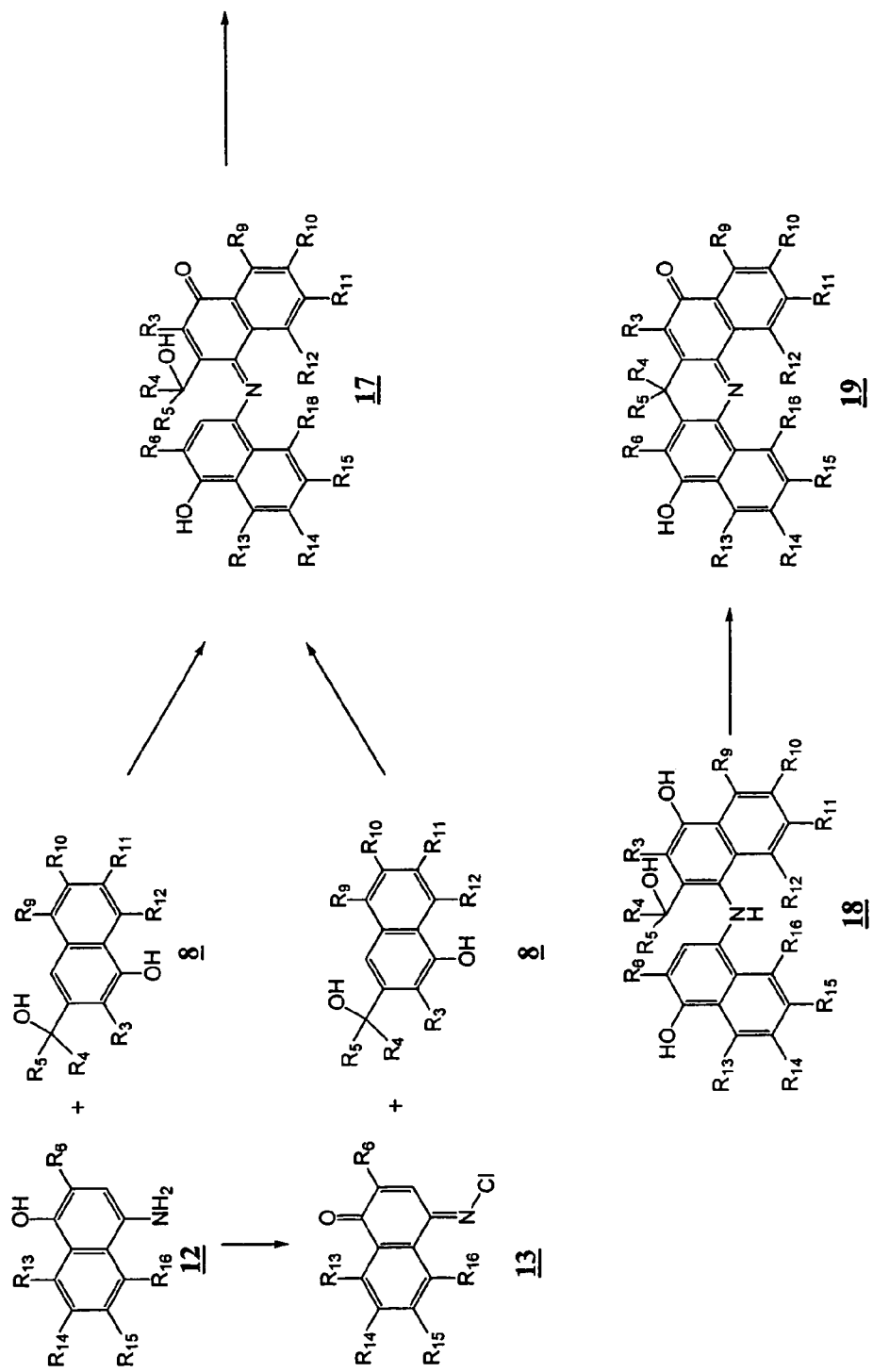
FIG. 4 shows a generalized synthetic pathway for the synthesis of dye compounds of the present teachings comprising the structure (IV).

An exemplary synthetic scheme for the preparation of compounds of the present teachings comprising the structure (IV) is shown in FIG. 4. Following a scheme similar to that described by Corey, a compound of the type (12) can be reacted with a tertiary alcohol (8), in the presence of a base to form compound (17). Alternatively, compound (12) can be oxidized using known conditions to form an N-chloroimine compound of the type (13) which can be reacted with a tertiary alcohol (8) in the presence of a base to form compound (17). Compound (17) can then be reacted with a reducing agent, such as sodium dithionite, to form secondary amine compound (18). Compound (18) can then be converted to compound (19) by cyclization, through treatment with an acid such as 2N HCl, followed by oxidation, with for example sodium periodate. In some embodiments, depending on the substitution pattern present, compound (19) can optionally be further derivitized. For example, compound (19) can optionally be sulfonated by reaction with, for example, chlorosulfonic acid.

Figure 5:
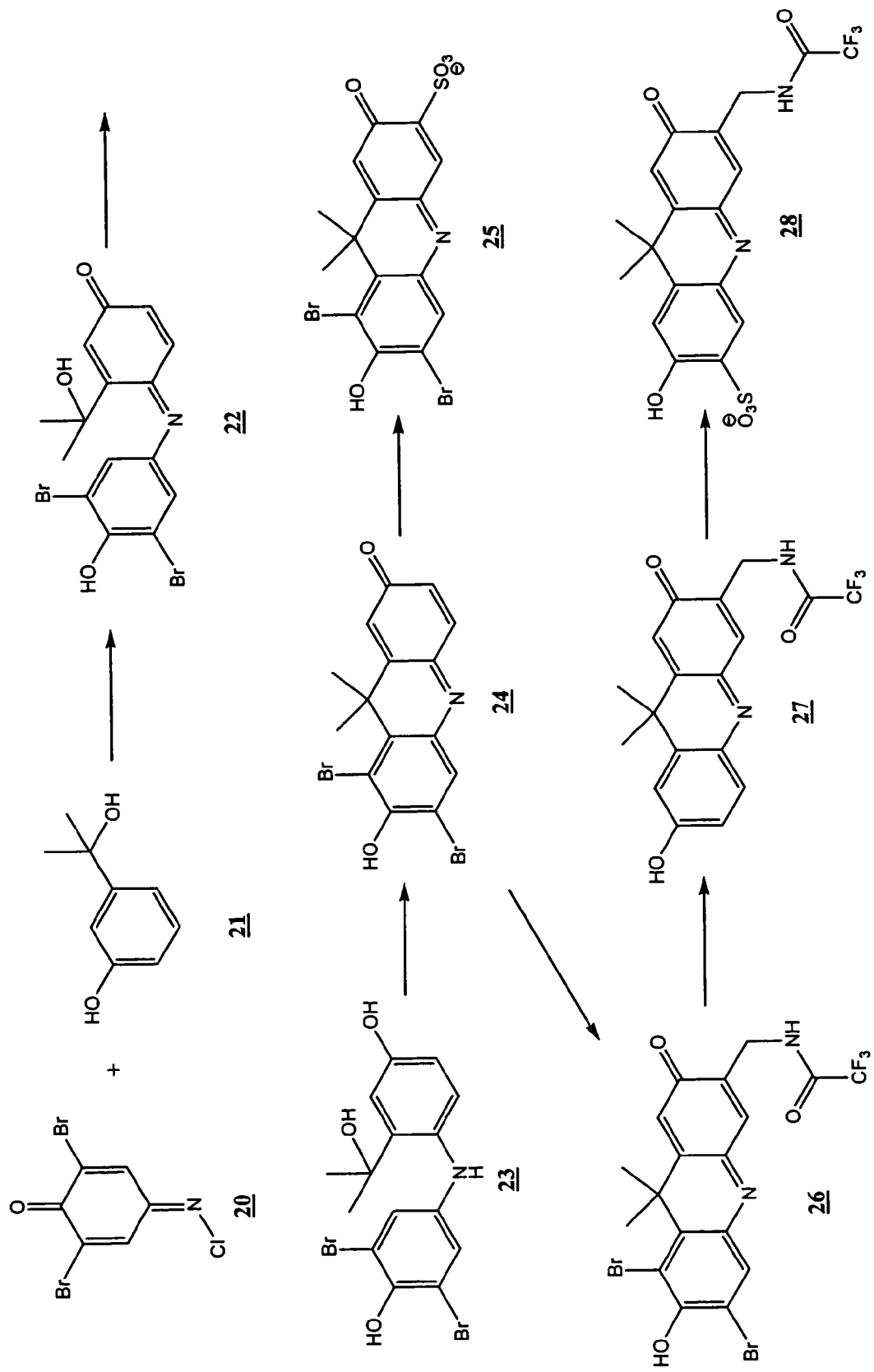
FIG. 5 shows a possible synthetic pathway for the synthesis of dye compounds of the present teachings comprising the structure (I).

A synthetic scheme for the preparation of exemplary compounds of the present teachings is shown in FIG. 5. Following a scheme similar to that described by Corey, a chloroimine compound of the type (20) can be reacted with a tertiary alcohol (21), in the presence of a base to form compound (22). Compound (2) can then be reacted with a reducing agent, such as sodium dithionite, to form secondary amine compound (23). Compound (23) can then be converted to compound (24) by cyclization, through treatment with an acid such as 2N HCl, followed by oxidation, with for example sodium periodate. Further, compound (24) can be sulfonated by reaction with, for example, chlorosulfonic acid to provide dye (25) of the present teachings. Alternatively, compound (24) can be aminomethylated by reaction with an aminomethylating agent, for example, N-(hydroxymethyl)trifluoroacetamide in the presence of an acid such as concentrated sulfuric acid, or similar established conditions to form compound (26). Dye (26) can be dehalogenated by literature procedure (Corey, P. F., U.S. Pat. No. 4,810,636 Mar. 7, 1989; Corey, et al. Angew Chem Int. Ed. Engl 30 (1991)), by reduction with, for example, Raney nickel/$H_2$ and then oxidized by reacting with an oxidizing agent, such as sodium periodate, to give dye (27) of the present teachings. Dye (27) can be can be sulfonated by reaction with, for example, chlorosulfonic acid to provide dye (28) of the present teachings.

If one of skill in the art were to use 2-(4'-hydroxynathalen-2-yl)-2-propanol as the tertiary alcohol, it could be prepared according to the literature procedures (Haworth et al. *J. Chem Soc, Abstracts*, pp. 10-13 (1943)), see FIG. 6. Specifically, benzyl succinate (29) (commercially available from Sigma-Aldrich Chemical Company, Milwaukee, Wis.) can be suspended in cold acetyl chloride to give a bis-anhydride benzyl succinate derivative. The anhydride derivative can be cyclized to the tetralone intermediate with $AlCl_3$ in nitrobenzene. The tetralone intermediate can be aromatized in two steps by bromination and base catalyzed bromide elimination to give 4-hydroxy-2-napthoic acid (30). 4-Hydroxy-2-napthoic acid compound (30) can be converted to the ethyl ester derivative by Fisher esterification in ethanol and HCl. Finally, using established literature procedures (*J. Am. Chem. Soc.*, v. 108, 4119 (1986)), ethyl 4-Hydroxy-2-napthoate can be reacted with methyl magnesium chloride (3.3 eqiuv) to give the tertiary alcohol 2-(4'-hydroxynathalen-2-yl)-2-propanol (31).

Figure 7:
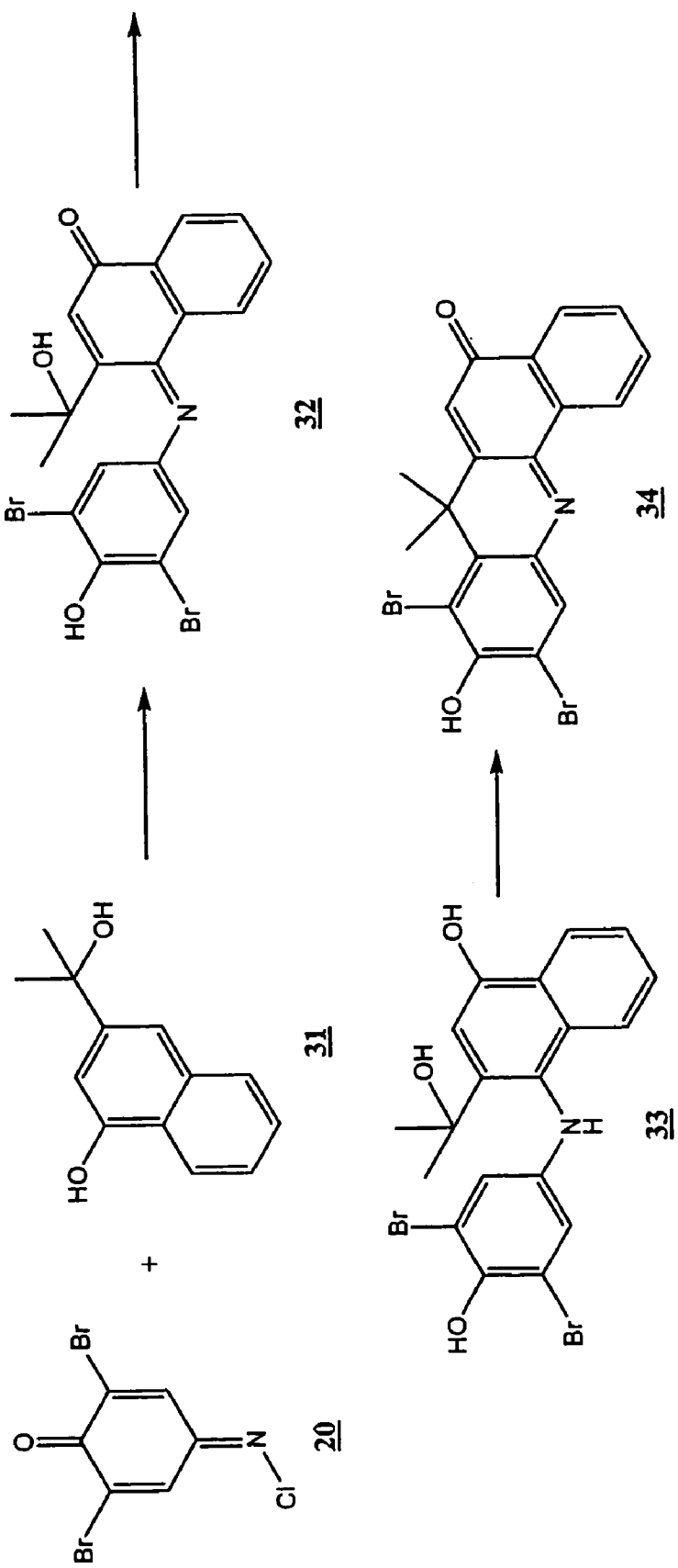
FIG. 7 shows a possible synthetic scheme for the preparation of compounds of the present teachings comprising the structure (II).

A synthetic scheme for the preparation of exemplary compounds of the present teachings is shown in FIG. 7. Following a scheme similar to that described by Corey, N-chloroimine compound (20) can be reacted with tertiary alcohol (31), in the presence of a base to form compound (32). Compound (32) can then be reacted with a reducing agent, such as sodium dithionite, to form secondary amine compound (33). Compound (33) can then be converted to compound (34) by cyclization, through treatment with an acid such as 2N HCl, followed by oxidation, with for example sodium periodate.

Figure 8:
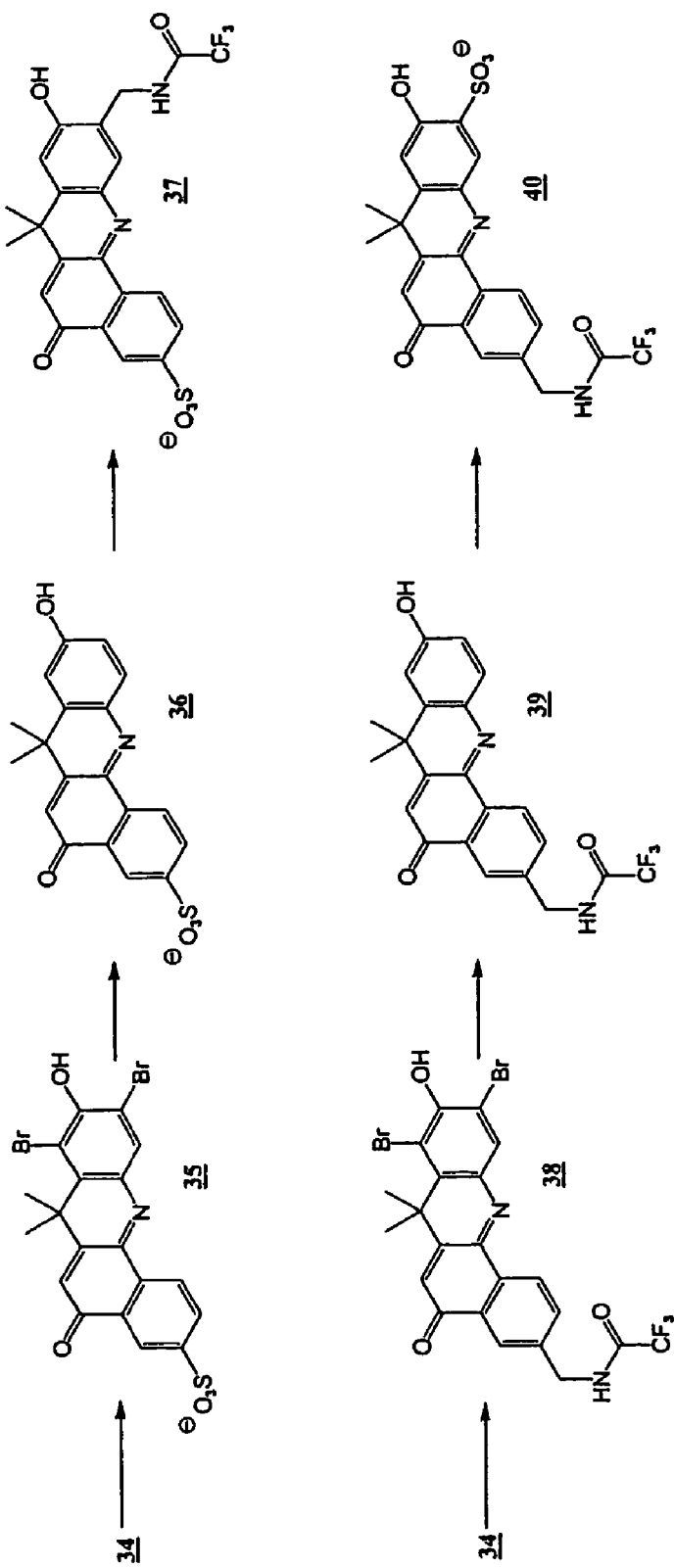
FIG. 8 shows possible synthetic schemes for the preparation of compounds of the present teachings comprising the structure (II).
Figure 9:
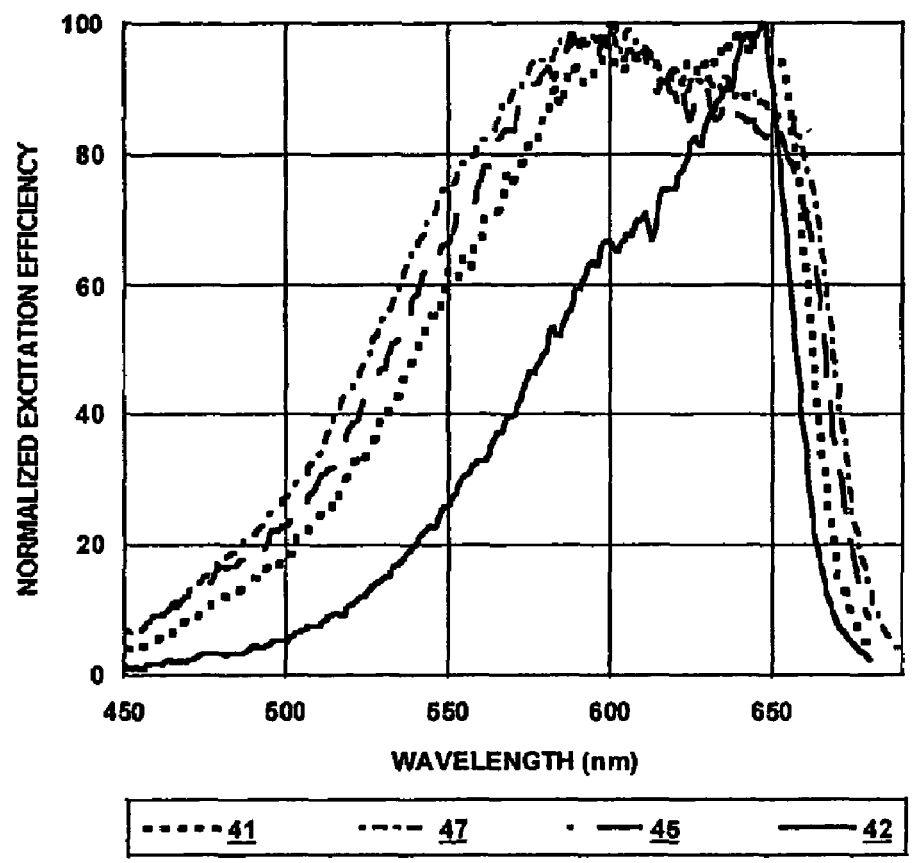
FIG. 9 shows absorption spectra of DDAO and several representative compounds of the present teachings.
Figure 10:
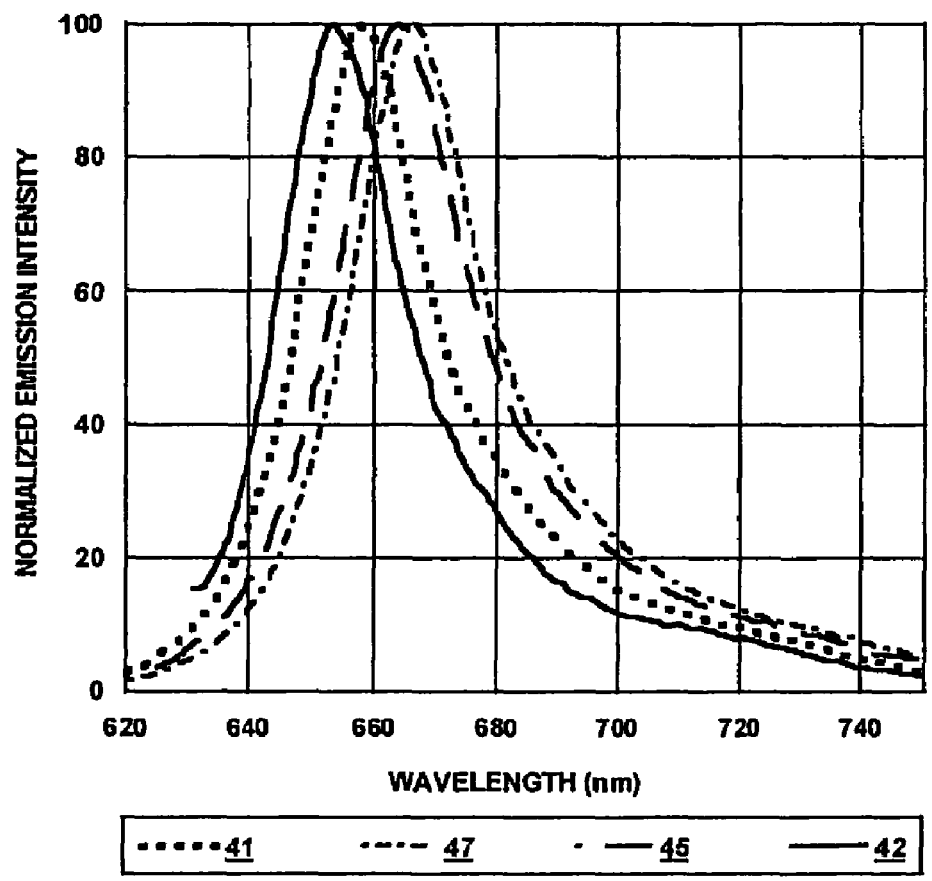
FIG. 10 shows emission spectra of DDAO and several representative compounds of the present teachings.

A synthetic scheme for the conversion of exemplary compound (34) to further compounds of the present teachings is shown in FIG. 8. In some embodiments, dye (34) can be can be sulfonated by reaction with, for example, chlorosulfonic acid to provide dye (35) of the present teachings. Dye (35) can be de-halogenated by literature procedure (Corey, P. F., U.S. Pat. No. 4,810,636 Mar. 7, 1989; Corey, et al. Angew Chem Int. Ed. Engl. 30 (1991)), by reduction with, for example, Raney nickel/$H_2$ and then oxidized by reacting with an oxidizing agent, such as sodium periodate, to give dye (36) of the present teachings. Dye (36) can be aminomethylated by treating with N-(hydroxymethyl)trifluoroacetamide in the presence of an acid such as concentrated sulfuric acid, or similar established conditions to form compound (37) of the present teachings. Alternatively, dye (34) can be aminomethylated by treating with N-(hydroxymethyl)trifluoroacetamide in the presence of an acid such as concentrated sulfuric acid, or similar established conditions to form compound (38). As above, compound (38) can be de-halogenated and then oxidized by literature procedures to give compound (39). Finally, compound (39) can be sulfonated by reaction with, for example, chlorosulfonic acid to provide a dye (40) of the present teachings. Further, one of skill in the art will recognize that the amine functionality on compounds (37) or (40) can optionally be deprotected and optionally converted to a substituted amine and/or compounds (37) or (40) can optionally be halogenated using established procedures to tune the fluorescence properties (i.e. -emission wavelength).

Suitable N-chloroimine compounds of the type (3), shown in, for example, FIGS. 1 & 2, for use in connection with the present teachings can be obtained from commercial sources and/or prepared from numerous 4-hydroxyaniline compounds that are either commercially available or are known in the art using literature established procedures. Examples, of suitable 4-hydroxyaniline compounds include, but are not limited to, the following:

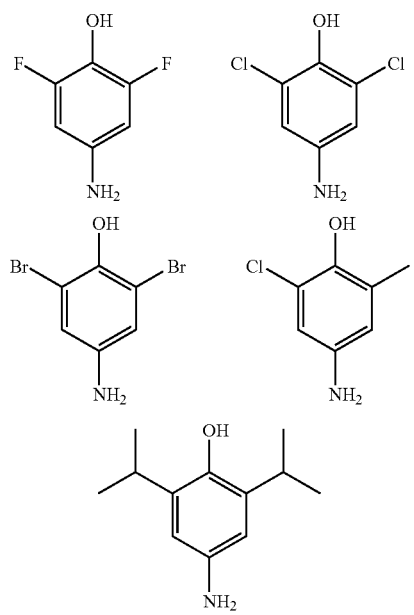

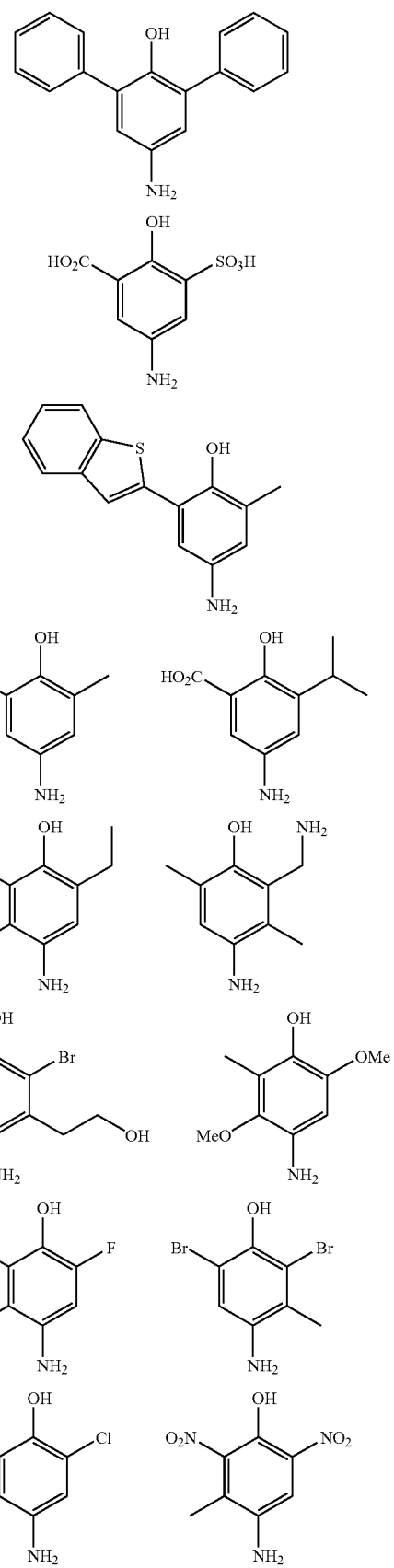

-continued

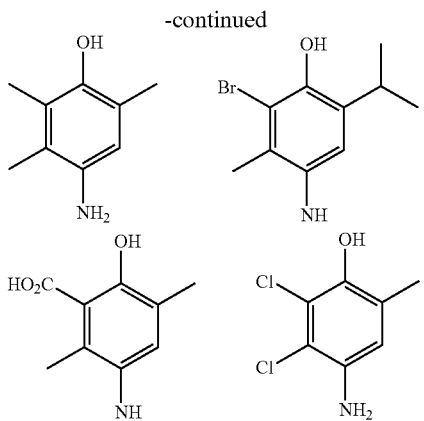

One of skill in the art will understand that any of the above 4-hydroxyaniline compounds can be converted into the N-chloroimine directly or after optional protection of possibly labile functionality. Further examples of suitable for 4-hydroxyaniline compounds that are known in the art can be found by structure searching in available databases such as Chemical Abstracts Service (CAS), SciFinder, and the like.

Suitable N-chloroimine compounds of the type (12), shown in, for example, FIG. 3, for use in connection with the present teachings can be obtained from commercial sources and/or prepared from numerous 4-hydroxy-aminonaphthalene compounds that are either commercially available or are known in the art using literature established procedures. Examples, of suitable 4-hydroxy-aminonaphthalene compounds include, but are not limited to, the following:

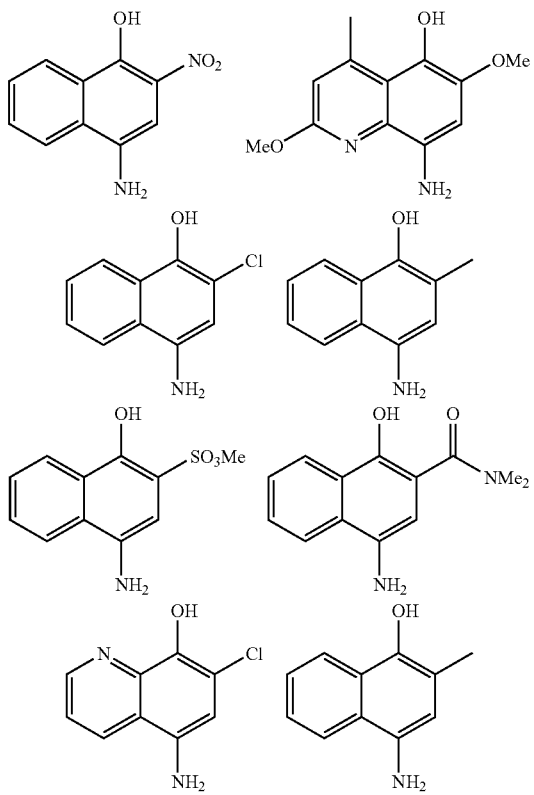

-continued

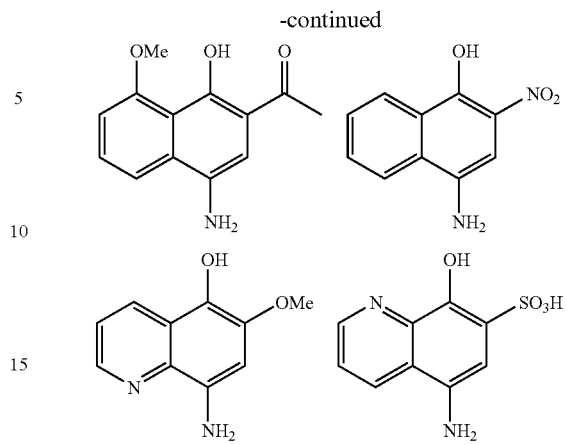

One of skill in the art will understand that any of the above 4-hydroxy-aminonaphthalene compounds can be converted into the N-chloroimine directly or after optional protection of possibly labile functionality. Further examples of suitable for 4-hydroxy-aminonaphthalene compounds that are known in the art can be found by structure searching in available databases such as Chemical Abstracts Service (CAS), SciFinder, and the like.

Figure 6:
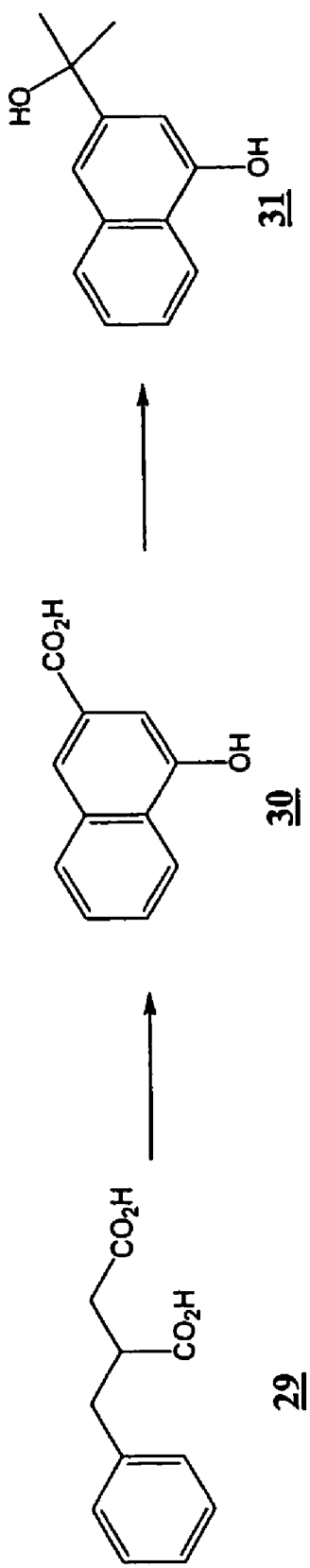
FIG. 6 shows an exemplary synthetic pathway for the synthesis of a tertiary alcohol (e.g. -2-(4'-hydroxynathalen-2-yl)-2-propanol) intermediate useful for the preparation of compounds of the present teachings.

Suitable tertiary alcohol compounds of the type (8) shown in, for example, FIG. 2, can be prepared from suitable 4-hydroxy-2-napthoic acid compounds in a manner similar to that described in FIG. 6. Examples of suitable 4-hydroxy-2-napthoic acid compounds known in the art include, but are not limited to, the following:

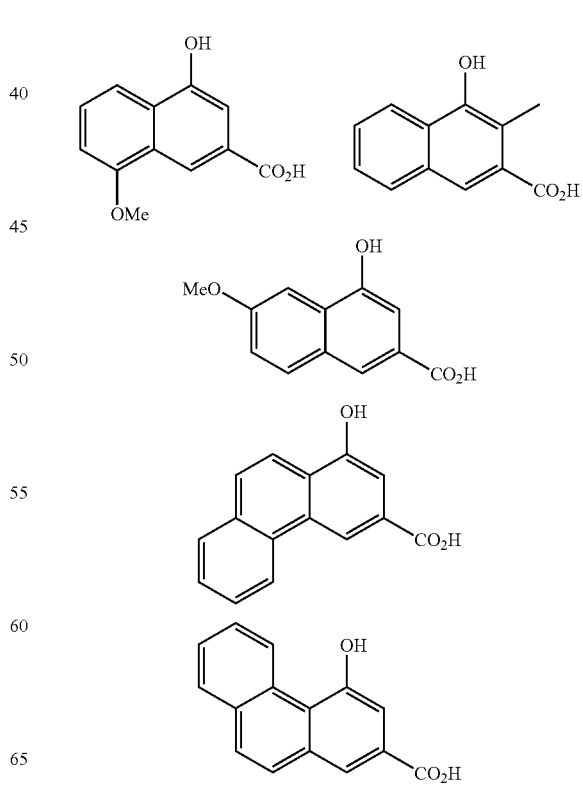

-continued

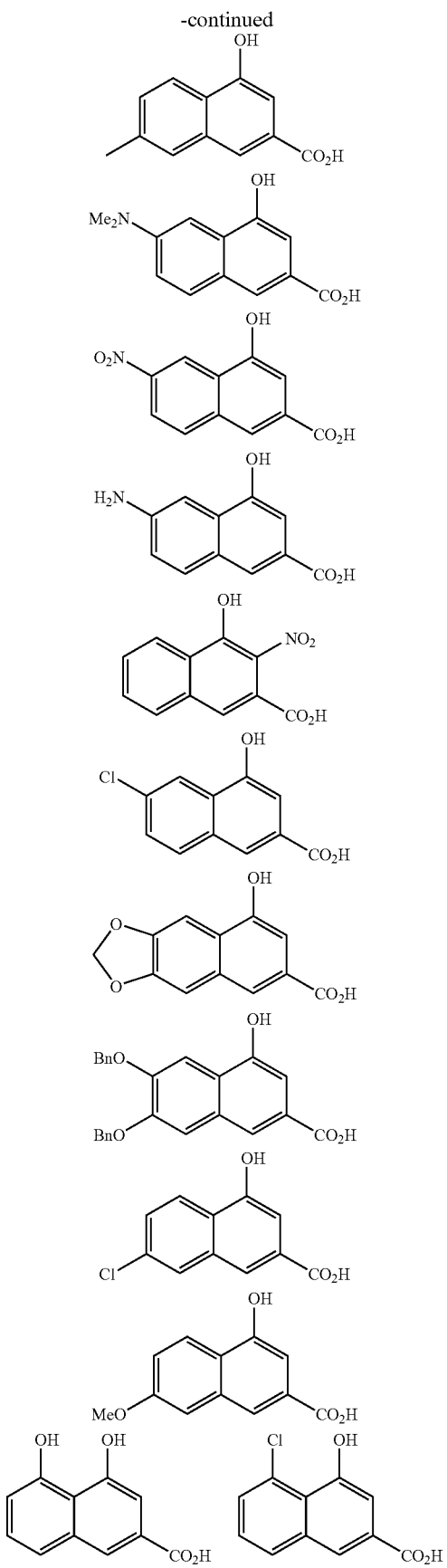

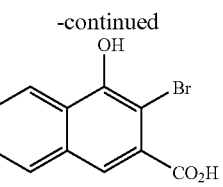

One of skill in the art will understand that any of the above 4-hydroxy-2-napthoic acid compounds can be used directly for synthesizing compounds of the present teachings or after optional protection of possibly labile functionality. Further examples of suitable for 4-hydroxy-2-napthoic acid compounds that are known in the art can be found by structure searching in available databases such as Chemical Abstracts Service (CAS), SciFinder, and the like.

In some embodiments, the present teachings comprise energy transfer dye compounds incorporating dye compounds of Formula I-IV. Generally, energy transfer dyes of the present teachings comprise a donor dye capable of absorbing light at a first wavelength and emitting excitation energy in response that is covalently attached to an acceptor dye which is capable of absorbing the excitation energy emitted by the donor dye and fluorescing at a second wavelength in response. In some embodiments, the donor dye can be covalently attached to the acceptor dye through a linker. In some embodiments, the linker can be effective to facilitate efficient energy transfer between the donor and acceptor dyes. In some embodiments, the linker can be non-nucleotidic. In some embodiments, the linker can be a nucleotidic linker, such as a polynucleotide. For a thorough discussion of the structure, synthesis and use of such energy transfer dyes see, for example, Mathies, et al. U.S. Pat. No. 5,728,528, Lee, et al. U.S. Pat. No. 5,863,727, Glazer, et al. U.S. Pat. No. 5,853,992, Waggoner, et al., U.S. Pat. No. 6,008,373, Nampalli, et al., U.S. Patent Application Pub. No. 2004/0126763 A1, Kumar, et al., PCT Pub. No. WO 00/13026A1 and PCT Pub. No. WO 01/19841A1, each of which is incorporated herein by reference for all it discloses with regard to energy transfer dye structures, energy transfer dye synthesis, energy transfer dye linkers, alternative donor dyes, alternative acceptor dyes and energy transfer dye spectral properties.

In some embodiments, linkers suitable for use in connection with the present teachings can comprise the general structure

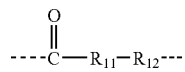

wherein carbonyl can be covalently attached to either a donor dye or an acceptor dye, $R_{11}$ can be a moiety that comprises an unsubstituted alkene, a substituted alkene, an unsubstituted diene, a substituted diene, an unsubstituted triene, a substituted triene, an unsubstituted alkyne, a substituted alkyne, an unsubstituted five- or six-membered ring having at least one unsaturated bond, a substituted five- or six-membered ring having at least one unsaturated bond or an unsubstituted or substituted fused ring structure that is attached to the carbonyl carbon atom, and $R_{12}$ is a moiety comprising a functional group that is capable of attaching the linker to a donor dye or an acceptor dye, such that both a donor dye and an acceptor dye are represented.

Examples of suitable five- or six-membered rings that can be used as $R_{11}$ in the linker include, but are not limited to cyclopentene, cyclohexene, cyclopentadiene, cyclohexadiene, furan, thiofuran, pyrrole, pyrazole, isoimidazole, pyran, pyrone, benzene, pyridine, pyridazine, pyrimidine, triazine, pyrazine and oxazine. Examples of fused ring structures include, but are not limited to indene, benzofuran, thionaphthalene, indole and naphthalene. In some embodiments, the linker has the structure

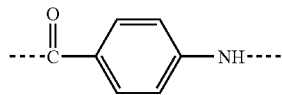

In some embodiments, the linker attaches to a dye of the present teachings at one of the $X_1$-$X_2$, $R_1$-$R_3$ or $R_7$-$R_{10}$ positions. In some embodiments, the linker can be a bond. Additional suitable linkers include polynucleotides, ribonucleic acids, and the like.

In some embodiments, one of the donor or acceptor dye is a dye according to the present teachings and the other dye can be a cyanine, phthalocyanine, squaraine, bodipy, fluorescein, rhodamine, extended rhodamine or dibenzorhodamine dye.

Example of suitable dyes for use in connection with energy transfer dyes of the present teachings include, but are not limited to, 5-carboxyfluorescein, 6-carboxyfluorescein, rhodamine green (R110), 5-carboxyrhodamine, 6-carboxyrhodamine, N,N'-diethyl-2',7'-dimethyl-5-carboxyrhodamine (5-R6G), N,N'-diethyl-2',7'-dimethyl-6-carboxyrhodamine (6-R6G), N,N,N',N'-tetramethyl-5-carboxyrhodamine (5-TAMRA), N,N,N',N'-tetramethyl-5-carboxyrhodamine (6-TAMRA), 5-carboxy-X-rhodamine (5-ROX), 6-carboxy-X-rhodamine (6-ROX), 5-carboxy-2',4',5',7',4,7-hexachlorofluorescein, 6-carboxy-2',4',5',7',4,7-hexachloro-fluorescein, 5-carboxy-2',7'-dicarboxy-4',5'-dichlorofluorescein, 6-carboxy-2',7'-dicarboxy-4',5'-dichloro-fluorescein, 5-carboxy-2',4',5',7'-tetrachlorofluorescein, 1',2'-benzo-4'-fluoro-7',4,7-trichloro-5-carboxyfluorescein, 1',2'-benzo-4'-fluoro-7',4,7-trichloro-6-carboxyfluorescein, 1',2',7',8'-dibenzo-4,7-dichloro-5-carboxyfluorescein, as well as other commercially available dyes as shown in Table 2.

TABLE 2

| Fluorescent Dye | Absorbance (nm) | Emission (nm) | Extinction Coefficient |
|---|---|---|---|
| 5-Fluorescein | 495 | 520 | 73000 |
| 5-Carboxyfluorescein (5-FAM) | 495 | 520 | 83000 |
| 6-Carboxyfluorescein (6-FAM) | 495 | 520 | 83000 |
| 6-Carboxyhexachloro-fluorescein (6-HEX) | 535 | 556 | 73000 |
| 6-Carboxytetrachloro-fluorescein (6-TET) | 521 | 536 | 73000 |
| JOE | 520 | 548 | 73000 |
| LightCycler Red 640 | 625 | 640 | |
| LightCycler Red 705 | 685 | 705 | |
| Oregon Green 488 | 496 | 516 | 76000 |
| Oregon Green 500 | 499 | 519 | 84000 |
| Oregon Green 514 | 506 | 526 | 85000 |
| BODIPY FL-X | 504 | 510 | 70000 |
| BODIPY FL | 504 | 510 | 70000 |
| BODIPY-TMR-X | 544 | 570 | 56000 |
| BODIPY R6G | 528 | 547 | 70000 |
| BODIPY 650/665 | 650 | 665 | 101000 |
| BODIPY 564/570 | 563 | 569 | 142000 |
| BODIPY 581/591 | 581 | 591 | 136000 |
| BODIPY TR-X | 588 | 616 | 68000 |
| BODIPY 630/650 | 625 | 640 | 101000 |
| BODIPY 493/503 | 500 | 509 | 79000 |
| 5-Carboxyrhodamine 6G | 524 | 557 | 102000 |

TABLE 2-continued

| Fluorescent Dye | Absorbance (nm) | Emission (nm) | Extinction Coefficient |
|---|---|---|---|
| 5(6)-Carboxytetramethyl-rhodamine (TAMRA) | 546 | 576 | 90000 |
| 6-Carboxytetramethyl-rhodamine (TAMRA) | 544 | 576 | 90000 |
| 5(6)-Carboxy-X-Rhodamine (ROX) | 576 | 601 | 82000 |
| 6-Carboxy-X-Rhodamine (ROX) | 575 | 602 | 82000 |
| AMCA-X (Coumarin) | 353 | 442 | 19000 |
| Texas Red-X | 583 | 603 | 116000 |
| Rhodamine Red-X | 560 | 580 | 129000 |
| Marina Blue | 362 | 459 | 19000 |
| Pacific Blue | 416 | 451 | 37000 |
| Rhodamine Green-X | 503 | 528 | 74000 |
| 7-diethylaminocoumarin-3-carboxylic acid | 432 | 472 | 56000 |
| 7-methoxycoumarin-3-carboxylic acid | 358 | 410 | 26000 |
| Cy3 | 552 | 570 | 150000 |
| Cy3B | 558 | 573 | 130000 |
| Cy5 | 643 | 667 | 250000 |
| Cy5.5 | 675 | 694 | 250000 |
| DY-505 | 505 | 530 | 85000 |
| DY-550 | 553 | 578 | 122000 |
| DY-555 | 555 | 580 | 100000 |
| DY-610 | 606 | 636 | 140000 |
| DY-630 | 630 | 655 | 120000 |
| DY-633 | 630 | 659 | 120000 |
| DY-636 | 645 | 671 | 120000 |
| DY-650 | 653 | 674 | 77000 |
| DY-675 | 674 | 699 | 110000 |
| DY-676 | 674 | 699 | 84000 |
| DY-681 | 691 | 708 | 125000 |
| DY-700 | 702 | 723 | 96000 |
| DY-701 | 706 | 731 | 115000 |
| DY-730 | 734 | 750 | 113000 |
| DY-750 | 747 | 776 | 45700 |
| DY-751 | 751 | 779 | 220000 |
| DY-782 | 782 | 800 | 102000 |
| Cy3.5 | 581 | 596 | 150000 |
| EDANS | 336 | 490 | 5700 |
| WellRED D2-PA | 750 | 770 | 170000 |
| WellRED D3-PA | 685 | 706 | 224000 |
| WellRED D4-PA | 650 | 670 | 203000 |
| Pyrene | 341 | 377 | 43000 |
| Cascade Blue | 399 | 423 | 30000 |
| Cascade Yellow | 409 | 558 | 24000 |
| PyMPO | 415 | 570 | 26000 |
| Lucifer Yellow | 428 | 532 | 11000 |
| NBD-X | 466 | 535 | 22000 |
| Carboxynapthofluorescein | 598 | 668 | 42000 |
| Alexa Fluor 350 | 346 | 442 | 19000 |
| Alexa Fluor 405 | 401 | 421 | 35000 |
| Alexa Fluor 430 | 434 | 541 | 16000 |
| Alexa Fluor 488 | 495 | 519 | 71000 |
| Alexa Fluor 532 | 532 | 554 | 81000 |
| Alexa Fluor 546 | 556 | 573 | 104000 |
| Alexa Fluor 555 | 555 | 565 | 150000 |
| Alexa Fluor 568 | 578 | 603 | 91300 |
| Alexa Fluor 594 | 590 | 617 | 73000 |
| Alexa Fluor 633 | 632 | 647 | 100000 |
| Alexa Fluor 647 | 650 | 665 | 239000 |
| Alexa Fluor 660 | 663 | 690 | 132000 |
| Alexa Fluor 680 | 679 | 702 | 184000 |
| Alexa Fluor 700 | 702 | 723 | 192000 |
| Alexa Fluor 750 | 749 | 775 | 240000 |
| Oyster 556 | 556 | 570 | 155000 |
| Oyster 645 | 645 | 666 | 250000 |
| Oyster 656 | 656 | 674 | 220000 |
| 5(6)-Carboxyeosin | 521 | 544 | 95000 |
| Erythrosin | 529 | 544 | 90000 |

In some embodiments, the present teachings provide for labeled nucleosides and/or nucleotides comprising the structure

NUC-L-D wherein NUC comprises a nucleoside, a nucleotide, a modified nucleoside or a modified nucleotide, L comprises a bond or a linker and D comprises a dye compound of the present teachings. In some embodiments, NUC and D can be conjugated by a linker, L, wherein L can be attached to D at one of $X_1$-$X_2$, $R_1$-$R_3$ or $R_7$-$R_{10}$. In some embodiments, if NUC comprises a purine base, the linker can be attached to the 8-position of the purine, if NUC comprises a 7-deazapurine base, the linker can be attached to the 7-position of the 7-deazapurine, and if NUC comprises a pyrimidine base, the linker can be attached to the 5-position of the pyrimidine. Such nucleoside and nucleotide reagents can be particularly useful in the context of labeling polynucleotides formed by enzymatic synthesis, e.g., nucleotide triphosphates used in the context of PCR amplification, Sanger-type polynucleotide sequencing, and nick-translation reactions.

It will be understood that nucleoside labeling can be accomplished by any of number of known labeling techniques employing known linkers, linking groups, and associated complementary functionalities. Generally, the linker should (i) not interfere with oligonucleotide-target hybridization, (ii) be compatible with relevant enzymes, e.g., polymerases, ligases, and the like, and (iii) not adversely affect the fluorescence properties of the dye. For exemplary base labeling procedures suitable for use in connection with the present teachings see, for example, Gibson, et al., *Nucleic Acids Research*, 15:6455-6467 (1987); Gebeyehu, et al., *Nucleic Acids Research*, 15: 4513-4535 (1987); Haralambidis, et al., *Nucleic Acids Research*, 15: 4856-4876 (1987); Nelson, et al., *Nucleosides and Nucleotides*, 5(3): 233-241 (1986); Bergstrom, et al., *JACS*, 111: 374-375 (1989); and U.S. Pat. Nos. 4,855,225, 5,231,191, and 5,449,767.

In some embodiments, suitable linkers can be acetylenic amido or alkenic amido linkers, wherein the conjugation between the dye and the nucleoside or nucleotide base can be formed by, for example, reaction of an activated N-hydroxysuccinimide (NHS) ester of the dye with an alkynylamino- or alkenylamino-derivatized base of a nucleoside or nucleotide. In some embodiments, labeled nucleosides or nucleotides can comprise the structure

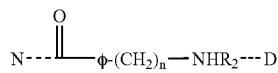

In some embodiments, labeled nucleosides or nucleotides can comprise the structure

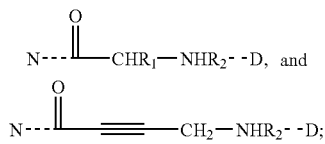

wherein X can be

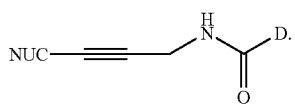

where n ranges from 1 to 5,

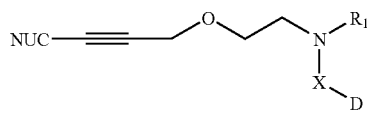

where n ranges from 1 to 5,

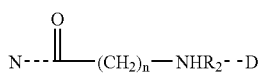

wherein $R_1$ can be —H or lower alkyl; and $R_2$ can be —H, lower alkyl or protecting group. See, for example, Khan et al., U.S. patent application Ser. No. 08/833,854 filed Apr. 10, 1997.

The synthesis of alkynylamino-derivatized nucleosides is taught by, for example, Hobbs, et al. in European Patent No. 0 251 786 B1, and Hobbs, et al., *J. Org. Chem.*, 54: 3420 (1989). Briefly, the alkynylamino-derivatized nucleotides can be formed by placing the appropriate halodideoxynucleoside (usually 5-iodopyrimidine and 7-iodo-7-deazapurine dideoxynucleosides as taught by Hobbs, et al. (cited above)) and Cu(I) in a flask, flushing with argon to remove air, adding dry DMF, followed by addition of an alkynylamine, triethylamine and Pd(0). The reaction mixture is stirred for several hours, or until thin layer chromatography indicates consumption of the halodideoxynucleoside. When an unprotected alkynylamine is used, the alkynylamino-nucleoside can be isolated by concentrating the reaction mixture and purifying by silica gel chromatography with an eluting solvent that contains ammonium hydroxide to neutralize hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

In some embodiments, nucleosides and/or nucleotides of the present teachings can comprise natural sugars (i.e. -ribose, 2'-deoxyribose, and the like) or sugar analogues. As used herein, the term "sugar analog" refers to analogs of the sugar ribose. Exemplary ribose sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NRR or halogen groups, where each R is independently —H, ($C_1$-$C_6$) alkyl or ($C_1$-$C_{14}$) aryl. Examples of substituted furanoses having 5 ring atoms include but are not limited to 2'-deoxyribose, 2'-($C_1$-$C_6$)alkylribose, 2'-($C_1$-$C_6$) alkoxyribose, 2'-($C_5$-$C_{14}$)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-($C_1$-$C_6$)alkylribose, 2'-deoxy-3'-($C_1$-$C_6$)

alkoxyribose, 2'-deoxy-3'-($C_5$-$C_4$)aryloxyribose, 3'-($C_1$-$C_6$) alkylribose-5'-triphosphate, 2'-deoxy-3'-($C_1$-$C_6$)alkylribose-5'-triphosphate, 2'-deoxy-3'-($C_1$-$C_6$)alkoxyribose-5'-triphosphate, 2'-deoxy-3'-($C_5$-$C_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate. Further sugar analogs also include so called locked nucleic acids (LNAs) having the structure

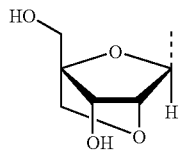

and those described in Wengel, et al. WO 99/14226, incorporated herein by reference.

In some embodiments, nucleosides and/or nucleotides of the present teachings can have the structure

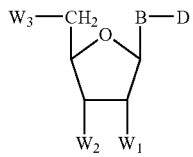

wherein B comprises a nucleoside or nucleotide base, such as uracil, cytosine, deazaadenine, or deazaguanosine; $W_1$ and $W_2$ taken separately can be —OH or a group capable of blocking polymerase-mediated template-directed polymerzation, e.g., —H, fluorine, and the like; $W_3$ can be OH, or mono-, di- or triphosphate or a phosphate analog; and D is a dye compound of the present teachings. In some embodiments, nucleotides of the present teachings can be dideoxynucleotide triphosphates having the structure including associated counterions if present.

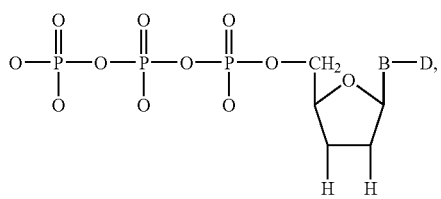

including associated counterions if present.

Labeled dideoxy nucleotides such as that shown above find particular application as chain terminating agents in Sanger-type DNA sequencing methods utilizing fluorescent detection.

In some embodiments, nucleotides of the present teachings can be deoxynucleotide triphosphates having the structure

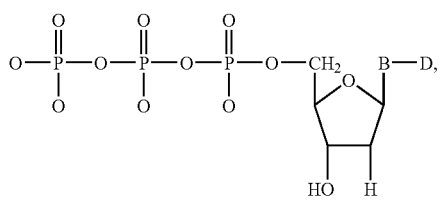

including associated counterions if present.

Labeled deoxynucleotides such as that shown above find particular application as reagents for labeling polymerase extension products, e.g., in the polymerase chain reaction or nick-translation.

In some embodiments, the present teachings can provide polynucleotides labeled with at least one dye of the present teachings. Such labeled polynucleotides are useful in a number of important contexts including as DNA sequencing primers, PCR primers, oligonucleotide hybridization probes, oligonucleotide ligation probes, and the like.

In some embodiments, labeled polynucleotides of the present teachings can include multiple dyes located such that fluorescence energy transfer takes place between a donor dye and an acceptor dye. Such multi-dye energy-transfer polynucleotides find application as spectrally-tunable sequencing primers, see for example, Ju, et al., *Proc. Natl. Acad. Sci. USA* 92: 4347-4351 (1995), or as hybridization probes, see for example, Lee, et al. *Nucleic Acids Research*, 21: 3761-3766 (1993).

Labeled polynucleotides can be synthesized either enzymatically, e.g., using a DNA polymerase or ligase, see for example, Stryer, *Biochemistry*, Chapter 24, W.H. Freeman and Company (1981), or by chemical synthesis, e.g., by the phosphoramidite method, the phosphitetriester method, and the like, see for example, Gait, *Oligonucleotide Synthesis*, IRL Press (1990). Labels may be introduced during enzymatic synthesis utilizing labeled nucleotide triphosphate monomers as described above, or introduced during chemical synthesis using labeled non-nucleotide or nucleotide phosphoramidites as described above, or may be introduced subsequent to synthesis.

Generally, if the labeled polynucleotide is made using enzymatic synthesis, the following procedure can be used. A template DNA is denatured and an oligonucleotide primer is annealed to the template DNA. A mixture of deoxynucleotide triphosphates is added to the mixture including dGTP, dATP, dCTP, and dTTP where at least a fraction of the deoxynucleotides is labeled with a dye compound of the invention as described above. Next, a polymerase enzyme is added under conditions where the polymerase enzyme is active. A labeled polynucleotide is formed by the incorporation of the labeled deoxynucleotides during polymerase-mediated strand synthesis. In an alternative enzymatic synthesis method, two primers are used instead of one, one primer complementary to the (+) strand and the other complementary to the (−) strand of the target, the polymerase is a thermostable polymerase, and the reaction temperature is cycled between a denaturation temperature and an extension temperature, thereby exponentially synthesizing a labeled complement to the target sequence by PCR, see for example, *PCR Protocols*, Innis et al. eds., Academic Press (1990).

Labeled polynucleotides can be chemically synthesized using the phosphoramidite method. Detailed descriptions of the chemistry used to form polynucleotides by the phosphoramidite method are provided in, for example, Caruthers et al., U.S. Pat. Nos. 4,458,066 and 4,415,732; Caruthers, et al., *Genetic Engineering*, 4: 1-17 (1982); *Users Manual Model 392 and 394 Polynucleotide Synthesizers*, pages 6-1 through 6-22, Applied Biosystems, Part No. 901237 (1991).

The phosphoramidite method of polynucleotide synthesis can be advantageous in some embodiments because of its efficient and rapid coupling reactions and the stability of the starting materials. The synthesis is performed with the growing polynucleotide chain attached to a solid support, so that excess reagents, which are in the liquid phase, can be easily removed by filtration, thereby eliminating the need for purification steps between synthesis cycles.

The following briefly describes the steps of a typical polynucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed that terminates any polynucleotide chains that did not undergo nucleoside addition. Capping can be accomplished with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, such as trichloroacetic acid or dichloroacetic acid, and the cycle is repeated until chain elongation is complete. After synthesis, the polynucleotide chain is cleaved from the support using a base, such as ammonium hydroxide or t-butyl amine. The cleavage reaction also removes any phosphate protecting groups, such as cyanoethyl. Finally, the protecting groups on the exocyclic amines of the bases and the hydroxyl protecting groups on the dyes are removed by treating the polynucleotide solution in base at an elevated temperature, e.g., 55° C. One of skill in the art will recognize that a variety if reagents can be used to perform the synthesis described above, and in some cases reagents are available to carry out more than one step in a single reaction.

Any of the phosphoramidite nucleoside monomers may be dye-labeled phosphoramidites as described above. If the 5'-terminal position of the nucleotide is labeled, a labeled non-nucleotidic phosphoramidite of the invention may be used during the final condensation step. If an internal position of the oligonucleotide is labeled, a labeled nucleotidic phosphoramidite of the invention may be used during any of the condensation steps.

Subsequent to synthesis, the polynucleotide may be labeled at a number of positions including the 5'-terminus, see for example *Oligonucleotides and Analogs,* Eckstein ed., Chapter 8, IRL Press (1991) and Orgel, et al., *Nucleic Acids Research* 11(18): 6513 (1983); U.S. Pat. No. 5,118,800; the phosphodiester backbone, see for example *Oligonucleotides and Analogs*, Eckstein ed., Chapter 9, IRL Press (1991); or at the 3'-terminus, see for example Nelson, *Nucleic Acids Research* 20(23): 6253-6259, and U.S. Pat. Nos. 5,401,837 and 5,141,813. For a through review of oligonucleotide labeling procedures see R. Haugland in *Excited States of Biopolymers*, Steiner ed., Plenum Press, NY (1983).

In one post-synthesis chemical labeling method an oligonuleotide can be labeled as follows. A dye including a carboxy linking group is converted to the N-hydroxysuccinimide ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10-20×) to an aminohexyl derivatized oligonucleotide in 0.25 M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylamine acetate (TEAA). The fraction containing the crude labeled oligonucleotide is further purified by reverse phase HPLC employing gradient elution.

It will be understood that the following examples are meant to be merely illustrative and are not meant to be limiting of the present teachings in any way. Although the above description will be adequate to teach one of skill in the art how to practice the present teachings, the following examples are provided as further guidance to those of skill in the art.

In some embodiments, the present teachings provide for a mixture comprising at least one compound of the present teachings in any of the forms described herein and at least one other component comprising a fluorescent dye. For example, the present teachings can provide for a mixture of polynucleotides, wherein at least one polynucleotide of the mixture comprises a compound of the present teachings and at least one other polynucleotide comprising a fluorescent dye. Mixture components comprising fluorescent dyes of the present teachings can be prepared by any of the methods described herein. In some embodiments, the present teachings provide for kits comprising at least one compound of the present teachings in any of the forms described herein.

EXAMPLES

Materials and Methods

Unless otherwise indicated, all reagents were obtained from Sigma-Aldrich (Milwaukee, Wis.) and used as received from the distributor. DDAO (1) was prepared as described in Corey, P. F., U.S. Pat. No. 4,810,636. NMR spectra were obtained using a Bruker 400 MHz Avance-NMR Spectrometer. Mass spec. data was obtained using an Applied Biosystems API 1500 Mass Spectrometer. Fluorescence data was obtained using a Perkin Elmer LS-50B Luminescence Spectrophotometer. UV/Vis data was obtained using a Hewlett Packard 8451A Diode Array Spectrophotometer.

Example 1

Synthesis of 6-sulfo-DDAO (42)

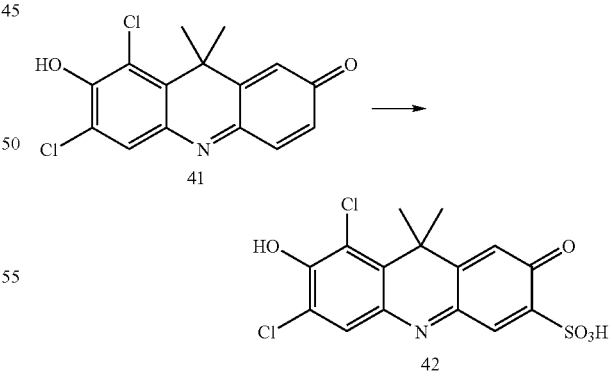

To a stirred solution of 50 mg of DDAO (41) dissolved in 5 mL dichloromethane (DCM) and cooled to 0° C. was added 0.5 mL chlorosulfonic acid. The reaction was stirred at 60° C. overnight and then poured into ice-water. Unreacted starting material was extracted with ethyl acetate (EtOAc) and then the product was extracted with n-butanol. The solvent was removed in vacou to obtain 45 mg of 6-sulfo-DDAO (42) as dark shiny crystals. $^1$H NMR (CD$_3$OD): δ 7.9 (s, 1H), 7.75 (s, 1H), 7.2 (s, 1H), 1.78 (s, 6H). MS: M+H=388.

Example 2

Synthesis of N-(4-caboxybenzoyl)-aminomethyl DDAO (45)

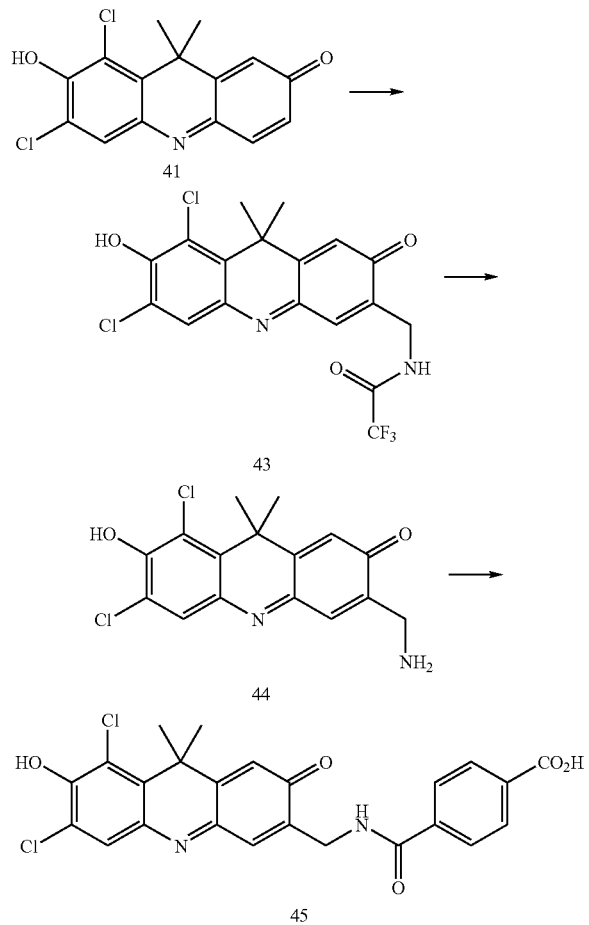

To a stirred solution of 450 mg DDAO (1.466 mmoles) in 10 mL of conc. sulfuric acid (H$_2$SO$_4$) was added 419 mg of N-(hydroxymethyl)trifluoroacetamide (2.929 mmoles) at room temperature. The resulting mixture was stirred at room temperature for 2 hours. The reaction was poured into 100 mL of ice water and extracted with 4×100 mL of 10% methanol/dichloromethane (MeOH/DCM). The organic layer was dried over sodium sulfate (Na$_2$SO$_4$), filtered and evaporated to dryness under reduced pressure. The residue was purified by silica gel chromatography using a gradient of 2:20:78 to 8:20:72 MeOH/ethyl acetate (EtOAc)/DCM) to give 456 mg of compound 43 as a reddish solid. $^1$H NMR (DMSO-d$_6$): δ 11.4 (br s, 1H, OH), 9.95 (t, 1H, NH), 7.82 (s, 1H), 7.34 (s, 1H), 7.03 (s, 1H), 4.35 (d, 2H), 1.78 (s, 6H). MS: (ESI) M-H=431.2.

A solution of 64 mg of compound 43 (0.148 mmoles) in 30 mL NH$_3$/MeOH was stirred at room temperature for 20 hours. The reaction was concentrated to dryness by evaporation and co-evaporation with MeOH. The solid was recrystallized from MeOH/DCM to give compound 44.

To a stirred solution of compound 44 in 6 mL dimethylformamide (DMF)/DCM (1:1) was added 118 mg of 4-carboxyethy terephthaloyl chloride (0.594 mmoles) and 0.2 mL diisopropylethylamine at room temperature. The resulting mixture was allowed to stir at room temperature for 3 hours. The reaction was then quenched by addition of 10 mL sat. aq. sodium bicarbonate (NaHCO$_3$) and 0.5 mL of a solution of sodium methoxide/MeOH (25%). The reaction mixture was then diluted with 20 mL H$_2$O and extracted 1×50 mL EtOAc. The organic layer was dried over Na$_2$SO$_4$, filtered and evaporated under reduced pressure. The residue was then treated with a solution of lithium hydroxide (LiOH)/MeOH/H$_2$O (177 mg/20 mL/5 mL) at 80° C. for 45 minutes. The reaction was then cooled to room temperature, evaporated under reduced pressure, re-dissolved in 30 mL H$_2$O, acidified with 1.5 mL 10% HCl, and extracted with 100 mL EtOAc. The organic layer was dried over Na$_2$SO$_4$, filtered and evaporated to dryness under reduced pressure. The residue was purified by silica gel chromatography (using a gradient of 1:9 to 8:2 MeOH/DCM) to give 52 mg of compound 45 as a solid. $^1$H NMR (DMSO-d$_6$): δ 8.84 (t, 1H, NH), 8.00 (d, 2H), 7.34 (m, 3H), 6.97 (s, 1H), 6.52 (s, 1H), 4.24 (d, 2H), 1.70 (s, 6H). MS: (ESI) M+H=485.0.

Example 3

Synthesis of 6,8-Dinitro-DDAO (46)

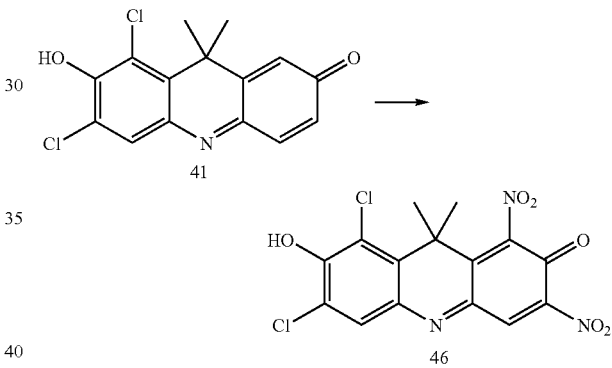

A solution of 50 mg of DDAO dissolved in 2 mL of a 1:1 solution of H$_2$SO$_4$/HNO$_3$ was stirred overnight at room temperature. The reaction was extracted with EtOAc. The solvent was removed in vacuo and the crude product was recrystallized from EtOH to give 41 mg of dinitro-DDAO (46).

Example 4

Synthesis of N-(4-carboxy-2-sulfobenzoyl)-aminomethyl DDAO (47)

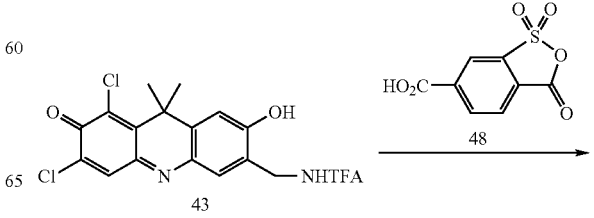

-continued

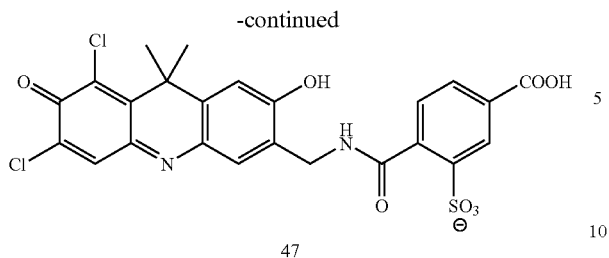

47

Compound 43 was prepared in the same manner as in Example 2. A solution of 43.3 mg of compound 43 (0.1 mmoles) in 20 mL NH$_3$/MeOH was stirred at room temperature for 20 hours. The reaction was concentrated to dryness by evaporation and co-evaporation with DCM to give compound 44.

The residue (44) was dissolved in 5 mL DMF and treated with 200 μL of diisopropylethylamine (Hunig's base) and 74 mg of anhydride 48 (0.324 mmoles) at room temperature. The reaction was stirred at room temperature for 3 hours then quenched with 1 mL 10% HCl. The solvent was removed in vacuo and the residue was redissolved in 50 mL H$_2$O and extracted with 3×50 mL 10% MeOH/EtOAc. The organic layer was dried over Na$_2$SO$_4$, filtered and evaporated to dryness.

The residue was then treated with 20 mL of a solution of LiOH.H$_2$O/MeOH/H$_2$O (0.85 g/100 mL/20 mL) at room temperature for 10 minutes. The mixture was acidified with 1 mL 10% HCl and diluted with 50 mL sat. NaCl. The mixture was extracted 2×100 mL 10% MeOH/EtOAc, then the organic layer was treated with 0.5 mL triethylamine, evaporated to dryness and finally co-evaporated with MeOH. The crude product was dissolved in 50 mL of 20% MeOH/DCM and purified by silica gel chromatography (2×17.5 cm, eluant gradient: 20%, 30%, 50%, 60%, 70% and 80% MeOH/DCM (100 mL each gradient step, collecting 20 mL fractions)) to give 60 mg of compound 47. $^1$H NMR (in MeOD): δ 8.52 (d, 1H), 8.01 (dd, 1H), 7.71 (d, 1H), 7.51 (s, 1H), 7.24 (s, 1H), 6.69 (s, 1H), 4.45 (s, 2H, CH$_2$), 1.82 (s, 6H, 2×CH$_3$). MS (ESI) m/e 563.2 (calcd. for M−H=563.0).

What is claimed is:

1. A compound having a structure selected from

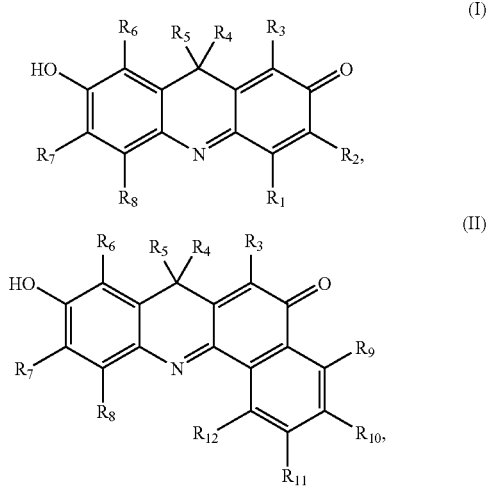

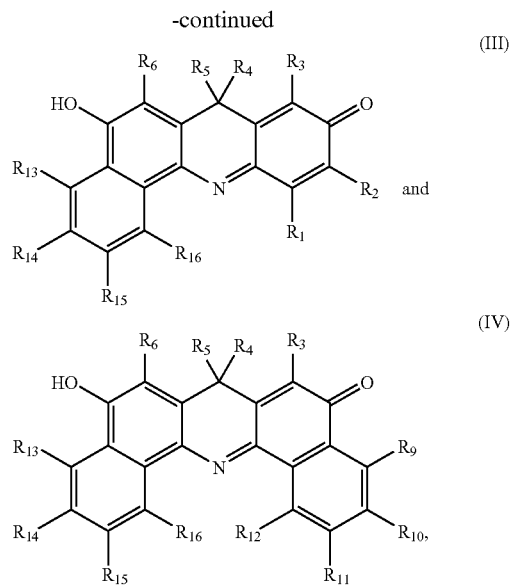

wherein

R$_1$-R$_3$ and R$_6$-R$_{16}$ are each independently selected from —H, halogen, heteroaryl, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR, —NO$_2$, C$_1$-C$_6$ alkyl, substituted C$_1$-C$_6$ alkyl, C$_1$-C$_6$ alkoxy, substituted C$_1$-C$_6$ alkoxy, C$_1$-C$_6$ alkoxyaryl, substituted C$_1$-C$_6$ alkoxyaryl, phenyl, substituted phenyl, biphenyl, substituted biphenyl, benzyl, substituted benzyl, benzoyl, substituted benzoyl, wherein R is selected from C$_1$-C$_6$ alkyl, substituted C$_1$-C$_6$ alkyl, C$_1$-C$_6$ alkoxy, substituted C$_1$-C$_6$ alkoxy, C$_1$-C$_6$ alkoxyaryl, substituted C$_1$-C$_6$ alkoxyaryl, phenyl, substituted phenyl, biphenyl, substituted biphenyl, benzyl, substituted benzyl, benzoyl, and substituted benzoyl; and R$_4$ and R$_5$ taken separately are selected from C$_1$-C$_6$ alkyl and C$_1$-C$_6$ substituted alkyl, R$_4$ and R$_5$ taken together are selected from C$_3$-C$_7$ cycloalkyl, C$_4$-C$_7$ unsaturated cycloalkyl, C$_3$-C$_7$ substituted cycloalkyl and C$_4$-C$_7$ substituted unsaturated cycloalkyl;

wherein or and R$_6$-R$_{16}$ is —SO$_3$H;

with the proviso that if the compound comprises the structure (I), then at least one of R$_1$, R$_2$, R$_3$ or R$_8$ is not —H.

2. The compound of claim 1, wherein R$_6$ and R$_7$ are each independently selected from fluorine, chlorine and bromine.

3. The compound of claim 2, wherein R$_6$ and R$_7$ are fluorine.

4. The compound of claim 2, wherein R$_6$ and R$_7$ are chlorine.

5. The compound of claim 2, wherein R$_6$ and R$_7$ are bromine.

6. The compound of claim 1, wherein R$_6$ is —H and R$_7$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, and —CH$_2$NHR.

7. The compound of claim 1, wherein R$_6$ is —H and R$_7$ is selected from —H, —SO$_3$H, —SO$_3$R, —CH$_2$CO$_2$H, —CH$_2$CO$_2$R, —CH$_2$NH$_2$, and —CH$_2$NHR.

8. The compound of claim 1, having structure (I), wherein R$_6$ and R$_7$ are each independently selected from fluorine, chlorine and bromine and R$_2$ is selected from —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$.

9. The compound of any one of claims 1-8, wherein the compound has the structure (I) and R$_2$ is selected from —SO$_3$H, —SO$_3$R, —CH$_2$NH$_2$, —CH$_2$NHR, and —NO$_2$.

10. The compound of any one of claims 1-8, wherein the compound has the structure (I) and R$_2$ is selected from —SO$_3$H and —SO$_3$R.

11. The compound of any one of claims 1-8, wherein the compound has the structure (I) and R$_2$ is selected from —CH$_2$NH$_2$ and —CH$_2$NHR.

12. The compound of claim 9, wherein R$_2$ is —SO$_3$H.
13. The compound of claim 9, wherein R$_2$ is —SO$_3$R.
14. The compound of claim 9, wherein R$_2$ is —CH$_2$NH$_2$.
15. The compound of claim 9, wherein R$_2$ is —CH$_2$NHR.
16. The compound of any one of claims 1-8, wherein R is

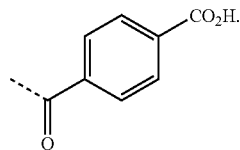

17. The compound of any one of claims 1, 6 or 7, wherein the compound has the structure (I), R$_7$ is —SO$_3$H and R$_2$ is —CH$_2$NH$_2$.

18. The compound of any one of claims 1, 6 or 7, wherein the compound has the structure (I), R$_7$ is —SO$_3$H and R$_2$ is —CH$_2$NHR.

19. The compound of claim 18, wherein R is substituted benzoyl.

20. The compound of claim 19, wherein R is

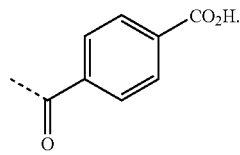

21. The compound of any one of claims 1-8, wherein R$_4$ and R$_5$ are methyl.

22. The compound of any one of claims 1-8, wherein R$_1$ and R$_3$ are —H.

23. The compound of claim 1, having structure (II), wherein R$_9$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$, and R$_3$ and R$_8$-R$_{10}$ are —H.

24. The compound of claim 23, wherein R$_9$ is selected from —SO$_3$H, —SO$_3$R, —CH$_2$NH$_2$, —CH$_2$NHR, and —NO$_2$.

25. The compound of claim 23, wherein R$_9$ is selected from —SO$_3$H and —SO$_3$R.

26. The compound of claim 23, wherein R$_9$ is selected from —CH$_2$NH$_2$ and —CH$_2$NHR.

27. The compound of claim 23, wherein R$_9$ is —SO$_3$H.
28. The compound of claim 23, wherein R$_9$ is —SO$_3$R.
29. The compound of claim 23, wherein R$_9$ is —CH$_2$NH$_2$.
30. The compound of claim 23, wherein R$_9$ is —CH$_2$NHR.

31. The compound of any one of claims 23-26, 28 or 30, wherein R is

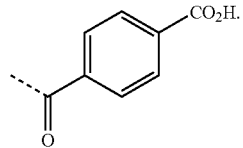

32. The compound of claim 6, having structure (II), wherein R$_9$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$, and R$_3$ and R$_{10}$-R$_{12}$ are —H.

33. The compound of claim 32, wherein R$_7$ is —SO$_3$H and R$_9$ is —CH$_2$NH$_2$.

34. The compound of claim 32, wherein R$_7$ is —SO$_3$H and R$_9$ is —CH$_2$NHR.

35. The compound of claim 32, wherein R is

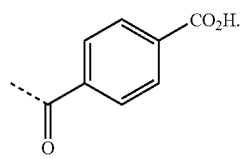

36. The compound of any claim 1, having structure (II), wherein R$_{10}$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$, and R$_3$, R$_9$ and R$_{11}$-R$_{12}$ are —H.

37. The compound of claim 36, wherein R$_{10}$ is selected from —SO$_3$H, —SO$_3$R, —CH$_2$NH$_2$, —CH$_2$NHR, and —NO$_2$.

38. The compound of claim 36, wherein R$_{10}$ is selected from —SO$_3$H and —SO$_3$R.

39. The compound of claim 36, wherein R$_{10}$ is selected from —CH$_2$NH$_2$ and —CH$_2$NHR.

40. The compound of claim 36, wherein R$_{10}$ is —SO$_3$H.
41. The compound of claim 36, wherein R$_{10}$ is —SO$_3$R.
42. The compound of claim 36, wherein R$_{10}$ is —CH$_2$NH$_2$.
43. The compound of claim 36, wherein R$_{10}$ is —CH$_2$NHR.

44. The compound of any one of claims 36-39, 41 or 43, wherein R is

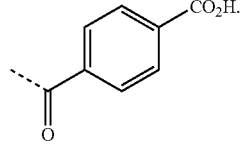

45. The compound of claim 6, having structure (II), wherein R$_{10}$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$ and R$_3$, R$_9$ and R$_{11}$-R$_{12}$ are —H.

46. The compound of claim 45, wherein R$_7$ is —SO$_3$H and R$_{10}$ is —CH$_2$NH$_2$.

47. The compound of claim 45, wherein $R_7$ is —SO$_3$H and $R_{10}$ is —CH$_2$NHR.

48. The compound of claim 47, wherein R is

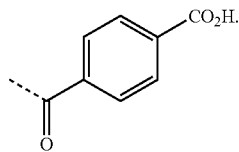

49. The compound of claim 1, having structure (II), wherein $R_{11}$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$, and $R_3$, $R_9$-$R_{10}$ and $R_{12}$ are —H.

50. The compound of claim 49, wherein $R_{11}$ is selected from —SO$_3$H, —SO$_3$R, —CH$_2$NH$_2$, —CH$_2$NHR, and —NO$_2$.

51. The compound of claim 49, wherein $R_{11}$ is selected from —SO$_3$H and —SO$_3$R.

52. The compound of claim 49, wherein $R_{11}$ is selected from —CH$_2$NH$_2$ and —CH$_2$NHR.

53. The compound of claim 49, wherein $R_{11}$ is —SO$_3$H.

54. The compound of claim 49, wherein $R_{11}$ is —SO$_3$R.

55. The compound of claim 49, wherein $R_{11}$ is —CH$_2$NH$_2$.

56. The compound of claim 49, wherein $R_{11}$ is —CH$_2$NHR.

57. The compound of any one of claims 49-52, 54 or 56, wherein R is

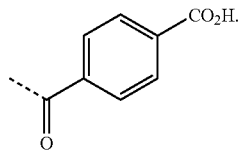

58. The compound of claim 6, having structure (II), wherein $R_{11}$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$, and $R_3$, $R_9$-$R_{10}$ and $R_{12}$ are —H.

59. The compound of claim 58, wherein $R_7$ is —SO$_3$H and $R_{11}$ is —CH$_2$NH$_2$.

60. The compound of claim 58, wherein $R_7$ is —SO$_3$H and $R_{11}$ is —CH$_2$NHR.

61. The compound of claim 60, wherein R is

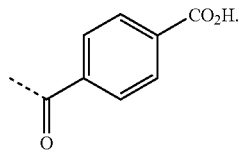

62. The compound of claim 1, having structure (II), wherein $R_{12}$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$, and $R_3$ and $R_9$-$R_{11}$ are —H.

63. The compound of claim 62, wherein $R_{12}$ is selected from —SO$_3$H, —SO$_3$R, —CH$_2$NH$_2$, —CH$_2$NHR, and —NO$_2$.

64. The compound of claim 62, wherein $R_{12}$ is selected from —SO$_3$H and —SO$_3$R.

65. The compound of claim 62, wherein $R_{12}$ is selected from —CH$_2$NH$_2$ and —CH$_2$NHR.

66. The compound of claim 62, wherein $R_{12}$ is —SO$_3$H.

67. The compound of claim 62, wherein $R_{12}$ is —SO$_3$R.

68. The compound of claim 62, wherein $R_{12}$ is —CH$_2$NH$_2$.

69. The compound of claim 62, wherein $R_{12}$ is —CH$_2$NHR.

70. The compound of any one of claims 62-65, 67 or 69, wherein R is

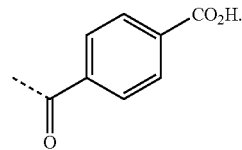

71. The compound of claim 6, having structure (II), wherein $R_{12}$ is selected from —H, —CO$_2$H, —CO$_2$R, —SO$_3$H, —SO$_3$R, —CH$_2$CO$_2$H, —CH$_2$CO$_2$R, —CH$_2$SO$_3$H, —CH$_2$SO$_3$R, —CH$_2$NH$_2$, —CH$_2$NHR and —NO$_2$, and $R_3$ and $R_9$-$R_{11}$ are —H.

72. The compound of claim 71, wherein $R_7$ is —SO$_3$H and $R_{12}$ is —CH$_2$NH$_2$.

73. The compound of claim 71, wherein $R_7$ is —SO$_3$H and $R_{12}$ is —CH$_2$NHR.

74. The compound of claim 73, wherein R is

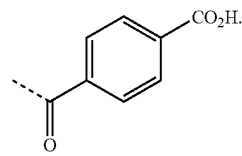

75. The compound of any one of claims 23, 32, 36, 45, 49, 58, 62 or 71, wherein $R_9$-$R_{12}$ are H.

76. The compound of any one of claims 23, 32, 36, 45, 49, 58, 62 or 71, wherein $R_4$ and $R_5$ are methyl.

77. The compound according to any one of claims 1-8, wherein $R_2$ and $R_3$ are —NO$_2$ and $R_4$ and $R_5$ are methyl.

78. The compound according to any one of claims 1, 6 or 7, having structure (III) and $R_1$ and $R_3$ are —H.

79. The compound of claim 78, wherein $R_6$ is —H.

80. The compound according to claim 78, wherein $R_{13}$, $R_{15}$ and $R_{16}$ are —H.

81. The compound of claim 80, wherein $R_2$ is —SO$_3$H.

82. The compound of claim 80, wherein $R_2$ is —H.

83. The compound according to claim 80, wherein $R_{14}$ is —CH$_2$NH$_2$.

84. The compound according to any one of claims 80-82, wherein $R_{14}$ is —CH$_2$NHR.

85. The compound of claim 84, wherein R is

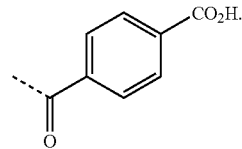

86. The compound of claim 81, wherein $R_{14}$ is —H.

87. The compound of claim 80, wherein $R_{14}$ is —SO$_3$H.

88. The compound of claim 80, wherein $R_{14}$ is —H.

89. The compound according to claim 80, wherein $R_2$ is —CH$_2$NH$_2$.

90. The compound according to claim 80, wherein $R_2$ is —CH$_2$NHR.

91. The compound of claim 90, wherein R is

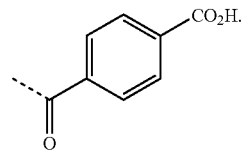

92. The compound of claim 87, wherein $R_2$ is —H.
93. The compound according to claim 89, wherein $R_4$ and $R_5$ are methyl.
94. The compound according to any one of claims 1, 6 or 7, wherein the compound has structure (IV).
95. The compound of claim 94, wherein $R_{14}$ is —$SO_3H$.
96. The compound of claim 94, wherein $R_{14}$ is —H.
97. The compound according to claim 94, wherein $R_{10}$ is —$CH_2NH_2$.
98. The compound according to claim 94, wherein $R_{10}$ is —$CH_2NHR$.
99. The compound of claim 98, wherein R is

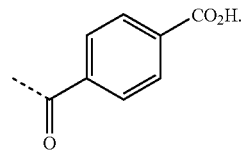

100. The compound according to claim 94, wherein $R_{14}$ is —H.
101. The compound according to claim 94, wherein $R_3$, $R_6$, $R_9$, $R_{11}$, $R_{12}$, $R_{13}$, $R_{15}$ and $R_{16}$ are —H.
102. The compound according to claim 94, wherein $R_4$ and $R_5$ are methyl.
103. A compound of claim 1 having the structure:

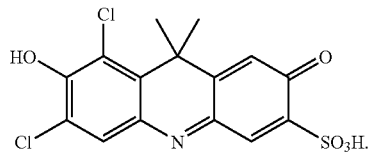

104. A compound of claim 1 having the structure:

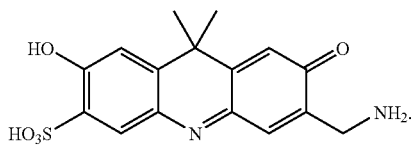

105. A compound of claim 1 having the structure:

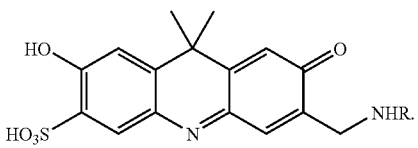

106. A compound of claim 1 having the structure

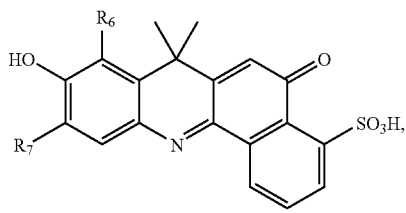

wherein $R_6$ and $R_7$ are each independently hydrogen, fluorine, chlorine or bromine.

107. A compound of claim 1 having the structure:

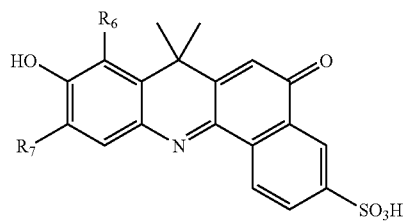

wherein $R_6$ and $R_7$ are each independently hydrogen, fluorine, chlorine or bromine.

108. A compound of claim 1 having the structure:

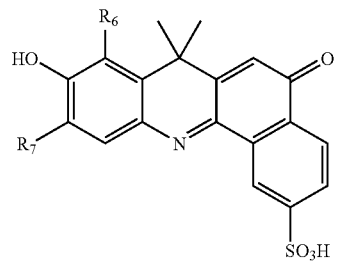

wherein $R_6$ and $R_7$ are each independently hydrogen, fluorine, chlorine or bromine.

109. A compound of claim 1 having the structure:

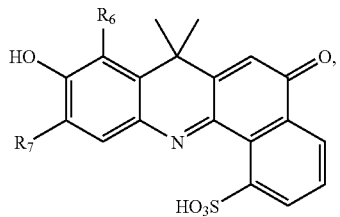

wherein $R_6$ and $R_7$ are each independently hydrogen, fluorine, chlorine or bromine.

110. A compound of claim 1 having the structure:
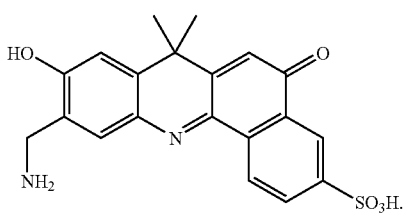
111. A compound of claim 1 having the structure:
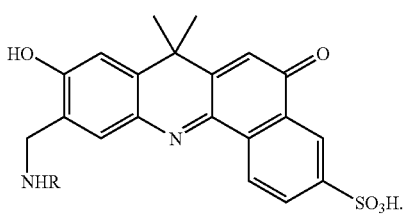
112. A compound of claim 1 having the structure:
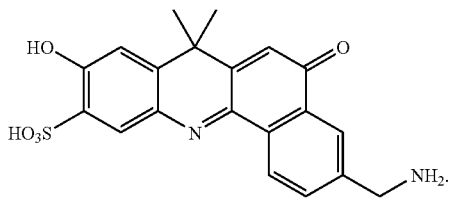
113. A compound of claim 1 having the structure:
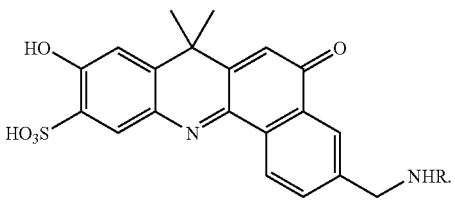
114. The compound of claim 82, wherein R14 is H.
* * * * *

UNITED STATES PATENT AND TRADEMARK OFFICE
CERTIFICATE OF CORRECTION

PATENT NO.      : 7,256,292 B2
APPLICATION NO. : 11/229012
DATED           : August 14, 2007
INVENTOR(S)     : Ronald Graham et al.

It is certified that error appears in the above-identified patent and that said Letters Patent is hereby corrected as shown below:

In the Claims

Claim 1, Column 35, lines 45 through 65, Column 36, lines 1 through 49, please replace with the one below:

1. A compound having a structure selected from

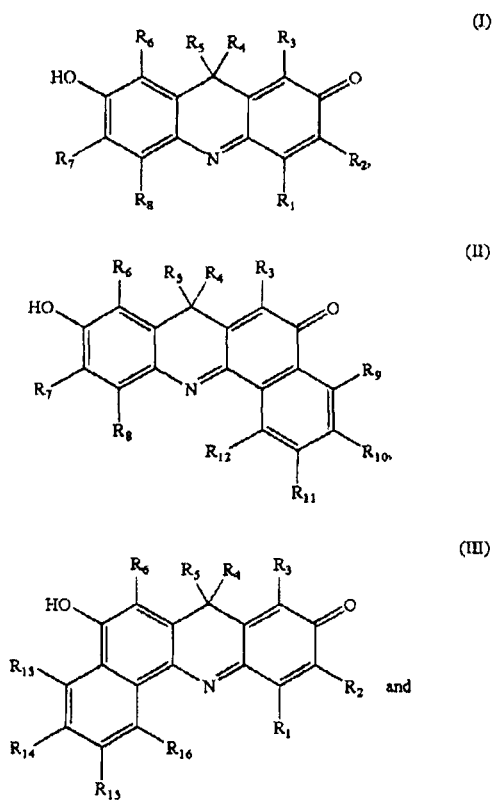

Signed and Sealed this
Twenty-fourth Day of March, 2015

Michelle K. Lee
*Director of the United States Patent and Trademark Office*

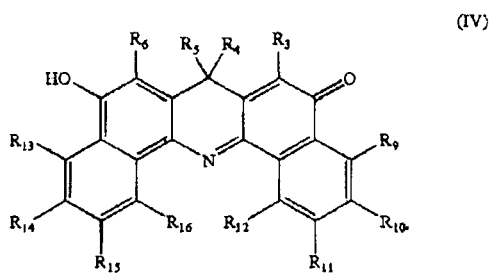

(IV)

wherein
$R_1$-$R_3$ and $R_6$-$R_{16}$ are each independently selected from —H, halogen, heteroaryl, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$, —$NO_2$, $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkoxyaryl, substituted $C_1$-$C_6$ alkoxyaryl, phenyl, substituted phenyl, biphenyl, substituted biphenyl, benzyl, substituted benzyl, benzoyl, substituted benzoyl, wherein R is selected from $C_1$-$C_6$ alkyl, substituted $C_1$-$C_6$ alkyl, $C_1$-$C_6$ alkoxy, substituted $C_1$-$C_6$ alkoxy, $C_1$-$C_6$ alkoxyaryl, substituted $C_1$-$C_6$ alkoxyaryl, phenyl, substituted phenyl, biphenyl, substituted biphenyl, benzyl, substituted benzyl, benzoyl, and substituted benzoyl; and
$R_4$ and $R_5$ taken separately are selected from $C_1$-$C_6$ alkyl and $C_1$-$C_6$ substituted alkyl, $R_4$ and $R_5$ taken together are selected from $C_3$-$C_7$ cycloalkyl, $C_4$-$C_7$ unsaturated cycloalkyl, $C_3$-$C_7$ substituted cycloalkyl and $C_4$-$C_7$ substituted unsaturated cycloalkyl;
wherein at least one of $R_1$-$R_3$ and $R_6$-$R_{16}$ is —$SO_3H$;
with the proviso that if the compound comprises the structure (I), then at least one of $R_1$, $R_2$, $R_3$ or $R_8$ is not —H.

Claim 36, Column 38, lines 31 through 35, please replace with the one below:

36. The compound of claim 1, having structure (II), wherein $R_{10}$ is selected from —H, —$CO_2H$, —$CO_2R$, —$SO_3H$, —$SO_3R$, —$CH_2CO_2H$, —$CH_2CO_2R$, —$CH_2SO_3H$, —$CH_2SO_3R$, —$CH_2NH_2$, —$CH_2NHR$ and —$NO_2$, and $R_3$, $R_9$ and $R_{11}$-$R_{12}$ are —H.

Claim 106, Column 42, lines 1 through 16, please replace with the one below:

106. A compound of claim 1 having the structure:

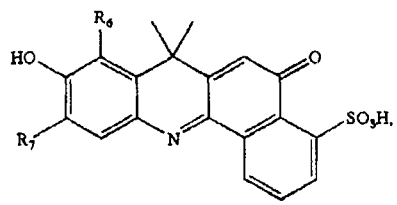

wherein $R_6$ and $R_7$ are each independently hydrogen, fluorine, chlorine or bromine.